United States Patent [19]
Berger et al.

[11] Patent Number: 5,641,668
[45] Date of Patent: Jun. 24, 1997

[54] PROTEINS HAVING GLYCOSYLTRANSFERASE ACTIVITY

[75] Inventors: Eric G. Berger, Schöfflisdorf, Switzerland; Manfred Watzele, Weilheim, Germany; Svetoslav X. Iwanow, Sofia, Bulgaria

[73] Assignee: CIBA-GEIGY Corporation, Tarrytown, N.Y.

[21] Appl. No.: 446,777

[22] PCT Filed: Nov. 15, 1994

[86] PCT No.: PCT/EP93/03194

§ 371 Date: May 26, 1995

§ 102(e) Date: May 26, 1995

[87] PCT Pub. No.: WO94/12646

PCT Pub. Date: Jun. 9, 1994

[30] Foreign Application Priority Data

Nov. 27, 1992 [EP] European Pat. Off. ............. 92810924

[51] Int. Cl.$^6$ .................. C12N 9/10; C12N 1/20; C12N 15/00; C07H 21/04
[52] U.S. Cl. .................. 435/193; 435/254.2; 435/320.1; 536/23.2; 536/23.4
[58] Field of Search .................. 435/69.1, 193, 435/254.2, 320.1; 536/23.2, 23.4

[56] References Cited

U.S. PATENT DOCUMENTS

| | | | |
|---|---|---|---|
| 5,032,519 | 7/1991 | Paulson et al. | 435/193 |
| 5,461,143 | 10/1995 | Wong et al. | 536/17.5 |
| 5,541,083 | 7/1996 | Paulson et al. | 435/41 |

FOREIGN PATENT DOCUMENTS

| | | |
|---|---|---|
| 4028-800-A | 9/1990 | Germany. |
| 2249096 | 4/1992 | United Kingdom. |
| WO90/07000 | 6/1990 | WIPO. |
| WO91/06635 | 5/1991 | WIPO. |
| WO91/12340 | 8/1991 | WIPO. |
| WO91/16900 | 11/1991 | WIPO. |

OTHER PUBLICATIONS

International Serach Report Dated Nov. 11, 1993.
Aoki, D., et al., "Analysis of the substrate binding sites of human galactosyltransferase by protein engineering", *The EMBO Journal*, 9(10):3171–3178 (1990).
Bitter, G.A., "[70] Heterologous Gene Expression in Yeast", *Meth. Enzymol.*, 152:673–684 (1987).
Chatterjee, S.K., "Molecular Cloning of Human β1,4–Galactosyltransferase and Expression of Catalytic Activity of the Fusion Protein in *Escherichia Coli*", *Int. J. Biochem.*, 23(7/8):695–702 (1991).
Colley, K.J., et al., "Conversion of a Golgi Apparatus Sialyltransferase to a Secretory Protein by Replacement of the NH$_2$–terminal Signal Anchor with a Signal Peptide*", *The Journal of Biological Chemistry*, 264(30):17619–17622 (1989).
Goelz, S.E., et al., "ELFT: A Gene That Directs the Expression of an ELAM–1 Ligand", *Cell*, 63:1349–1356 (1990).

Goodey, A.R., et al., "Expression and secretion of foreign polypeptides in yeast", *Yeast Biotechnology*, 401–429 (1987).
Grundmann, U., et al., "Complete cDNA sequence encoding human β–galactoside α–2,6–sialyltransferase", *Nucleic Acids Research*, 18(3):667 (1990).
Joziasse‡§, D. H., et al., "Bovine α1→3–Galactosyltransferase: Isolation and Characterization of cDNA Clone", *The Journal of Biological Chemistry*, 264(24):14290–14297 (1989).
Kidd, V.J., et al., "Complete Nucleotide Sequence and Biological Expression of Human 4β–Galactosyltransferase", *Fed. Proc.*, 46:2091 (1987).
Larsen, R.D., et al., "Molecular cloning, sequence, and expression of a human GDP-$_L$-fucose:β-$_D$-galactoside 2-α-$_L$fucosyltransferase cDNA that can from the H blood group antigen", *Proc. Natl. Acad. Sci. USA*, 87:6674–6678 (1990).
Lowe, J.B., "Molecular cloning, expression, and u ses of mammalian glycosyltransferases", *Cell Biology*, 2:289–307 (1991).
Masri, K.A., et al., "Identification of the Full–Length Coding Sequence For Human Galactosyltransferase (β–N–Acetyglucosaminide: β1,4–Galactosyltransferase)", *Biochemical and Biophysical Research Communications*, 157(2):657–663 (1988).
Munro, S., "Sequences within and adjacent to the transmembrane segment of α–2,6–sialyltransferase specify Golgi", *The EMBO Journal*, 10(12):3577–3588 (1991).
Nilsson, T., et al., "The membrane spanning domain of β–1,4–galactosyltransferase specifies trans Golgi localization", *The EMBO Journal*, 10(12):3567–3575 (1991).
Paulson, J.C., et al., "Expression of β–Galactoside α–2,6 Sialyltransferase in Chinese Hamster Ovary and Cos–1 Cells", *J. Biol. Chem.*, 264:17615–17618 (1989).
Paulson, J.C., et al., "Glycosyltransferase", *The Journal of Biological Chemistry*, 264(30):17615–17618 (1989).
Potvin‡§, B., et al., "Transfection of a Human α–(1,3)Fucosyltransferase Gene into Chinese Hamster Ovary Cells", *The Journal of Biological Chemistry*, 265(3):1615–1622 (1990).
Rademacher, T.W., "Therapeutic challenges: does Glycobiology have a role?", *Tibtech*, 10:227–30 (1992).
Shaper‡§, N.L., et al., "Characterization of the Full Length cDNA for Murine β–1,4–Galactosyltransferase", *The Journal of Biolocal Chemistry*, 263(21):10420–10428 (1988).

(List continued on next page.)

Primary Examiner—Robert A. Wax
Assistant Examiner—Lisa J. Hobbs
Attorney, Agent, or Firm—Gregory D. Ferraro; W. Murray Spruill

[57] ABSTRACT

The invention concerns proteins having glycosyltransferase activity, recombinant DNA molecules encoding proteins having glycosyltransferase activity, hybrid vectors comprising such recombinant DNA molecules, transformed hosts suitable for the multiplication and/or expression of the recombinant DNA molecules, and processes for the preparation of the proteins, DNA molecules and hosts.

9 Claims, No Drawings

OTHER PUBLICATIONS

Smith‡§, D.F., et al., "Transfer and Expression of a Murine UDP–Gal:β–$_D$–Gal–α1,3–Galactosyltransferase Gene in Transfected Chinese Hamster Ovary Cells", *The Journal of Biological Chemistry*, 265(11):6225–6234 (1990).

Toghrol, F., et al., "Expression of UDP–Glucuronosyltransferase cDNA in *Saccharomyces cerevisiae* as a Membrane–Bound and as a Cytosolic Form", *Biochemistry*, 23:349–2356 (1990).

Watzele, G., et al., "Near identity of HeLa cell galactosyltransferase with the human placental enzyme", *Nucleic Acids Research*, 18(23):7174 (1990).

Weinstein‡, J., et al., "Primary Structure of β–Galactoside α2,6–Sialyltransferase", *The Journal of Biological Chemistry*, 262(36):17735–17743 (1987).

Xu et al. (1996) Structure–Function Analysis of Human Alpha 1,3–Fucosyltransferase. J. Biol. Chem. 271(15):8818–8823.

PROTEINS HAVING GLYCOSYLTRANSFERASE ACTIVITY

The invention relates to proteins having glycosyltransferase activity and to a recombinant process for the production of proteins having glycosyltransferase activity.

Glycosyltransferases transfer sugar residues from an activated donor substrate, usually a nucleotide sugar, to a specific acceptor sugar thus forming a glycosidic linkage. Based on the type of sugar transferred, these enzymes are grouped into families, e.g. galactosyltransferases, sialyltransferases and fucosyltransferases. Being resident membrane proteins primarily located in the Golgi apparatus, the glycosyltransferase share a common domain structure consisting of a short amino-terminal cytoplasmic tail, a signal-anchor domain, and an extended stem region which is followed by a large carboxy-terminal catalytic domain. The signal-anchor or membrane domain acts as both uncleavable signal peptide and as membrane spanning region and orients the catalytic domain of the glycosyltransferase within the lumen of the Golgi apparatus. The luminal stem or spacer region is supposed to serve as a flexible tether, allowing the catalytic domain to glycosylate carbohydrate groups of membrane-bound and soluble proteins of the secretory pathway enroute through the Golgi apparatus. Furthermore, the stem portion was discovered to function as retention signal to keep the enzyme bound to the Golgi membrane (PCT Application No. 91/06635). Soluble forms of glycosyltransferases are found in milk, serum and other body fluids. These soluble glycosyltransferases are supposed to result from proteolytic release from the corresponding membrane-bound forms of the enzymes by endogenous proteases.

Glycosyltransferases are valuable tools for the synthesis or modification of glycoproteins, glycolipids and oligosaccharides. Enzymatic synthesis of carbohydrate structures has the advantage of high stereo- and regioselectivity. In contrast to chemical methods the time-consuming introduction of protective groups is superfluous. However, enzymatic synthesis of carbohydrate structures has been a problem because glycosyltransferases are not readily available. Therefore, production using recombinant DNA technology has been worked on. For example, galactosyltransferases have been expressed in *E. coli* (PCT 90/07000) and Chinese hamster ovary (CHO) cells (Smith, D. F. et al. (1990) J. Biol. Chem. 265, 6225-34), sialyltransferases have been expressed in CHO cells (Lee, E. U. (1990) Diss. Abstr. Int. B. 50, 3453-4) and COS-1 cells (Paulson, J. C. et al. (1988) J. Cell. Biol. 107, 10A), and fucosyltransferases have been produced in COS-1 cells (Goelz, S. E. et al. (1990) Cell 63, 1349-1356; Larsen R. D. et al. (1990) Proc. Natl. Acad. Sci. USA 87, 6674-6678) and CHO cells (Potvin, B. (1990) J. Biol. Chem. 265, 1615-1622). Recently, Paulson et al. have disclosed a method for producing soluble glycosyltransferases (U.S. Pat. No. 5,032,519). However, there still is a need for proteins having favorable glycosylating properties and for advantageous methods for producing such proteins.

It is an object of the present invention to provide novel proteins having glycosyltransferase activity, recombinant DNA molecules encoding proteins having glycosyltransferase activity, hybrid vectors comprising such recombinant DNA molecules, transformed hosts suitable for the multiplication and/or expression of the recombinant DNA molecules, and processes for the preparation of the proteins, DNA molecules and hosts.

The present invention concerns a protein having glycosyltransferase activity and comprising identical or different catalytically active domains of glycosyltransferases, e.g. hybrid proteins.

Preferred is a protein of the invention which comprises two identical or two different catalytically active domains of glycosyltransferases.

Particularly preferred is such a protein exhibiting two different glycosyltransferase activities, i.e. a protein capable of transferring two different sugar residues.

Besides the catalytically active domains a protein of the invention may comprise additional amino acid sequences, particularly amino acid sequences of the respective glycosyltransferases.

The invention also concerns a hybrid polypeptide chain, i.e. a hybrid protein, comprising a membrane-bound or soluble glycosyltransferase linked to a soluble glycosyltransferase. For example, such a hybrid protein comprises a membrane-bound glycosyltransferase linked to a soluble glycosyltransferase in N-to C-terminal order.

A glycosyltransferase is a protein exhibiting glycosyltransferase activity, i.e. transferring a particular sugar residue from a donor molecule to an acceptor molecule. Examples are N-acetylglucosaminyltransferases, N-acetylgalactosaminyltransferases, mannosyltransferases, fucosyltransferases, galactosyltransferases and sialyltransferases.

Preferably, the glycosyltransferase is of mammalian, e.g. bovine, murine, rat or, particularly, human origin.

Preferred are hybrid proteins exhibiting galactosyl- and sialyltransferase activity.

A membrane-bound glycosyltransferase is an enzyme which cannot be secreted by the cell it is produced by, e.g. a full-length enzyme. Examples of membrane-bound glycosyltransferases are the following galactosyltransferases: UDP-Galactose: β-galactoside α(1–3)-galactosyltransferase (EC 2.4.1.151 ) which uses galactose as acceptor substrate forming an α(1–3)-linkage and UDP-Galactose: α-N-acetylglucosamine α(1–4)-galactosyltransferase (EC 2.4.1.22) which transfers galactose to N-acetylglucosamine (GlcNAc) forming a α(1–4)-linkage. In the presence of α-lactalbumin, said β(1–4)-galactosyltransferase also accepts glucose as an acceptor substrate, thus catalysing the synthesis of lactose. An example of a membrane-bound sialyltransferase is the CMP-NeuAc: β-galactoside α(2–6)-sialyltransferase (EC 2.4.99.1) which forms the NeuAc-α (2–6)Gal-β(1–4)GlcNAc-sequence common to many N-linked carbohydrate groups.

A soluble glycosyltransferase is secretable by the host cell and is derivable from an N-terminally truncated full-length (i.e. a membrane-bound) glycosyltransferase naturally located in the Golgi apparatus. Such a soluble glycosyltransferase differs from the corresponding full-length enzyme by lack of the cytoplasmic tail, the signal anchor and, optionally, part or whole of the stem region. An example of soluble glycosyltransferases are galactosyltransferases differing from the protein with the amino acid sequence depicted in SEQ ID NO. 1 in that they lack an NH$_2$-terminal peptide comprising at least 41 amino acids. A soluble sialyltransferase is e.g. a sialyltransferase missing an NH$_2$-terminal peptide consisting of 26 to 61 amino acids as compared to the full length form depicted in SEQ ID No. 3.

As used hereinbefore and hereinafter the term "glycosyltransferase" is intended to include variants with the provision that these variants are enzymatically active. Preferred are variants of human origin.

For example, a variant is a naturally occurring variant of a glycosyltransferase found within a particular species, e.g. a variant of a galactosyltransferase which differs from the enzyme having the amino acid sequence with the SEQ ID NO. 1 in that it lacks serine in position 11 and has the amino acids valine and tyrosine instead of alanine and leucine in positions 31 and 32, respectively. Such a variant may be encoded by a related gene of the same gene family or by an allelic variant of a particular gene. The term "variant" also embraces a modified glycosyltransferase, e.g. a glycosyltransferase produced from a DNA which has been subjected to in vitro mutagenesis, with the provision that the protein encoded by said DNA has the enzymatic activity of the authentic glycosyltransferase. Such modifications may consist in an addition, exchange and/or deletion of one or more amino acids, the latter resulting in shortened variants. An example of a shortened membrane-bound, catalytically active variant is the galactosyltransferase designated $GT_{(1-396)}$ consisting of amino acids 1 to 396 of the amino acid sequence depicted in SEQ ID No. 1.

Preferred hybrid proteins comprise a membrane-bound or soluble glycosyltransferase linked to a soluble glycosyltransferase molecule, or a variant thereof, via a suitable linker consisting of genetically encoded amino acids. A suitable linker is a molecule which does not impair the favorable properties of the hybrid protein of the invention. The linker connects the C-terminal amino acid of one glycosyltransferase molecule with the N-terminal amino acid of the another glycosyltransferase molecule. For example, the linker is a peptide consisting of about 1 to about 20, e.g. of about 8 amino acids. In a preferred embodiment the linker, also referred to as adaptor, does not contain the amino acid cysteine. Particularly preferred is a peptide linker having the sequence Arg-Ala-Arg-Ile-Arg-Arg-Pro-Ala or Arg-Ala-Gly-Ile-Arg-Arg-Pro-Ala.

Preferred is a hybrid protein consisting of a galactosyltransferase linked to a sialyltransferase via a suitable peptide linker.

Particularly preferred is a hybrid protein consisting of a membrane-bound galactosyltransferase the C-terminal amino acid of which is linked to the N-terminal amino acid of a soluble sialyltransferase via a suitable peptide linker, e.g. a hybrid protein having the amino acid sequence set forth in SEQ ID NO. 6 or in SEQ ID NO. 8.

The hybrid protein according to the invention can be prepared by recombinant DNA techniques comprising culturing a suitable transformed yeast strain under conditions which allow the expression of the DNA encoding said hybrid protein. Subsequently, the enzymatic activity may be recovered.

In a preferred embodiment, the desired compounds are manufactured in a process comprising a) providing an expression vector comprising an expression cassette containing a DNA sequence coding for a hybrid protein,
b) transferring the expression vector into a suitable yeast strain,
c) culturing the transformed yeast strain under conditions which allow expression of the hybrid protein, and
d) recovering the enzymatic activity.

The steps involved in the preparation of the hybrid proteins by means of recombinant techniques will be discussed in more detail hereinbelow.

The invention further relates to a recombinant DNA molecule encoding a hybrid protein of the invention. Preferred are DNA molecules coding for the preferred hybrid proteins.

The nucleotide sequence encoding a particular glycosyltransferase is known from the literature or can be deduced from the amino acid sequence of the protein according to conventional rules. Starting from the nucleotide sequences encoding the desired glycosyltransferase activities, a DNA molecule encoding the desired hybrid protein can be deduced and constructed according to methods well known in the art including, but not limited to, the use of polymerase chain reaction (PCR) technology, DNA restriction enzymes, synthetic oligonucleotides, DNA ligases and DNA amplification techniques. Alternatively, the nucleotide sequence encoding the hybrid protein of the invention may be synthesized by chemical methods known in the art or by combining chemical with recombinant methods.

The DNA coding for a particular glycosyltransferase may be obtained from cell sources by conventional methods, e.g. by making use of cDNA technology, from vectors in the art or by chemical synthesis of the DNA.

More specifically, DNA encoding a membrane-bound glycosyltransferase can be prepared by methods known in the art and includes genomic DNA, e.g. DNA isolated from a mammalian genomic DNA library, e.g. from rat, murine, bovine or human cells. If necessary, the introns occurring in genomic DNA encoding the enzyme are deleted. Furthermore, DNA encoding a membrane-bound glycosyltransferase comprises cDNA which can be isolated from a mammalian cDNA library or produced from the corresponding mRNA. The cDNA library may be derived from cells from different tissues, e.g. placenta cells or liver cells. The preparation of cDNA via the mRNA route is achieved using conventional methods such as the polymerase chain reaction (PCR).

A DNA encoding a soluble glycosyltransferase is obtainable from a naturally occurring genomic DNA or a cDNA according to methods known in the art. For example, the partial DNA coding for a soluble form of a glycosyltransferase may be excised from the full-length DNA coding for the corresponding membrane-bound glycosyltransferase by using restriction enzymes. The availability of an appropriate restriction site is advantageous therefor.

Furthermore, DNA encoding a glycosyltransferase can be enzymatically or chemically synthesized.

A variant of a glycosyltransferase having enzymatic activity and an amino acid sequence in which one or more amino acids are deleted (DNA fragments) and/or exchanged with one or more other amino acids, is encoded by a mutant DNA. Furthermore, a mutant DNA is intended to include a silent mutant wherein one or more nucleotides are replaced with other nucleotides, the new codons coding for the same amino acid(s). Such a mutant sequence is also a degenerated DNA sequence. Degenerated DNA sequences are degenerated within the meaning of the genetic code in that an unlimited number of nucleotides are replaced by other nucleotides without resulting in a change of the amino acid sequence originally encoded. Such degenerated DNA sequences may be useful due to their different restriction sites and/or frequency of particular codons which are preferred by the specific host to obtain optimal expression of a glycosyltransferase. Preferably, such DNA sequences have the yeast preferred codon usage.

A mutant DNA is obtainable by in vitro mutation of a cDNA or of a naturally occurring genomic DNA according to methods known in the art.

The invention also concerns hybrid vectors comprising a DNA sequence encoding a hybrid protein of the invention. The hybrid vectors of the invention provide for replication and, optionally, expression of the DNA encoding a hybrid protein of the invention. A hybrid vector of the invention comprises a DNA sequence encoding a hybrid protein of the invention linked with an origin of replication allowing the replication of the vector in the host cell, or a functionally equivalent sequence. A vector suitable for the expression of the hybrid protein of the invention (an expression vector) comprises a DNA sequence encoding said hybrid protein operably linked with expression control sequences, e.g. promoters, which ensure the effective expression of the hybrid proteins in yeast, and an origin of replication allowing the replication of the vector in the host cell, or a functionally equivalent sequence.

Vectors suitable for replication and expression in yeast contain a yeast replication origin. Hybrid vectors that contain a yeast replication origin, for example the chromosomal autonomously replicating segment (ars), are retained extrachromosomally within the yeast cell after transformation and are replicated autonomously during mitosis. Also, hybrid vectors that contain sequences homologous to the yeast 2 μ plasmid DNA can be used. Such hybrid vectors are integrated by recombination in 2 μ plasmids already present within the cell, or replicate autonomously.

Preferably, the hybrid vectors according to the invention include one or more, especially one or two, selective genetic markers for yeast and such a marker and an origin of replication for a bacterial host, especially Escherichia coli.

As to the selective gene markers for yeast, any marker gene can be used which facilitates the selection for transformants due to the phenotypic expression of the marker gene. Suitable markers for yeast are, for example, those expressing antibiotic resistance or, in the case of auxotrophic yeast mutants, genes which complement host lesions. Corresponding genes confer, for example, resistance to the antibiotics G418, hygromycin or bleomycin or provide for prototrophy in an auxotrophic yeast mutant, for example the URA3, LEU2, LYS2 or TRP1 gene.

As the amplification of the hybrid vectors is conveniently done in E. coli, an E. coli genetic marker and an E. coli replication origin are included advantageously. These can be obtained from E. coli plasmids, such as pBR322 or a pUC plasmid, for example pUC 18 or pUC 19, which contain both E. coli replication origin and E. coli genetic marker conferring resistance to antibiotics, such as ampicillin.

An expression vector according to the invention comprises an expression cassette comprising a yeast promoter and a DNA sequence coding for hybrid protein of the invention, which DNA sequence is controlled by said promoter.

In a first embodiment, an expression vector according to the invention comprises an expression cassette comprising a yeast promoter, a DNA sequence coding for a hybrid protein, which DNA sequence is controlled by said promoter, and a DNA sequence containing yeast transcription termination signals.

In a second embodiment, the an expression vector according to the invention comprises an expression cassette comprising a yeast promoter operably linked to a first DNA sequence encoding a signal peptide linked in the proper reading frame to a second DNA sequence encoding a hybrid protein, and a DNA sequence containing yeast transcription termination signals.

The yeast promoter may be a regulated or a constitutive promoter preferably derived from a highly expressed yeast gene, especially a Saccharomyces cerevisiae gene. Thus, the promoter of the TRP1 gene, the ADHI or ADHIII gene, the acid phosphatase (PHO5) gene, a promoter of the yeast mating pheromone genes coding for the a- or α-factor or a promoter derived from a gene encoding a glycolytic enzyme such as the promoter of the enolase, glyceraldehyde-3-phosphate dehydrogenase (GAP), 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase or glucokinase genes can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PHO5 gene and downstream promoter elements including a functional TATA box of the yeast GAP. gene (PHO5-GAP hybrid promoter). Preferred is the PHO5 promoter, e.g. a constitutive PHO5 promoter such as a shortened acid phosphatase PHO5 promoter devoid of the upstream regulatory elements (UAS). Particularly preferred is the PHO5 (-173) promoter element starting at nucleotide -173 and ending at nucleotide -9 of the PHO5 gene.

The DNA sequence encoding a signal peptide ("signal sequence") is preferably derived from a yeast gene coding for a polypeptide which is ordinarily secreted. Other signal sequences of heterologous proteins, which are ordinarily secreted can also be chosen.

Yeast signal sequences are, for example, the signal and prepro sequences of the yeast invertase, α-factor, pheromone peptidase (KEX1), "killer toxin" and repressible acid phosphatase (PHO5) genes and the glucoamylase signal sequence from Aspergillus awamori. Alternatively, fused signal sequences may be constructed by ligating part of the signal sequence (if present) of the gene naturally linked to the promoter used (for example PHO5), with part of the signal sequence of another heterologous protein. Those combinations are favoured which allow a precise cleavage between the signal sequence and the glycosyltransferase amino acid sequence. Additional sequences, such as pro- or spacer-sequences which may or may not carry specific processing signals can also be included in the constructions to facilitate accurate processing of precursor molecules. Alternatively, fused proteins can be generated containing internal processing signals which allow proper maturation in vivo or in vitro. For example, the processing signals contain Lys-Arg, which is recognized by a yeast endopeptidase located in the Golgi membranes.

A DNA sequence containing yeast transcription termination signals is preferably the 3' flanking sequence of a yeast gene which contains proper signals for transcription termination and polyadenylation. Suitable 3' flanking sequences are for example those of the yeast gene naturally linked to the promoter used. The preferred flanking sequence is that of the yeast PHO5 gene.

If a hybrid protein comprising a membrane-bound glycosyltransferase is expressed in yeast, the preferred yeast hybrid vector comprises an expression cassette comprising a yeast promoter, a DNA sequence encoding said hybrid protein, which DNA sequence is controlled by said promoter, and a DNA sequence containing yeast transcription termination signals. If the DNA encodes a hybrid protein comprising a membrane-bound glycosyltransferase there is no need for an additional signal sequence.

In case the hybrid protein to be expressed comprises two soluble glycosyltransferases, the preferred yeast hybrid vector comprises an expression cassette comprising a yeast promoter operably linked to a first DNA sequence encoding a signal peptide linked in the proper reading frame to a second DNA sequence encoding hybrid protein and a DNA sequence containing yeast transcription termination signals.

The hybrid vectors according to the invention are prepared by methods known in the art, for example by linking the expression cassette comprising a yeast promoter and a DNA sequence coding for a glycosyltransferase, or a variant thereof, which DNA sequence is controlled by said promoter, or the several constituents of the expression cassette, and the DNA fragments containing selective genetic markers for yeast and for a bacterial host and origins of replication for yeast and for a bacterial host in the predetermined order, i.e. in a functional array.

The hybrid vectors of the invention are used for the transformation of the yeast strains described below.

The invention concerns furthermore a yeast strain which has been transformed with a hybrid vector of the invention.

Suitable yeast host organisms are strains of the genus Saccharomyces, especially strains of *Saccharomyces cerevisiae*. Said yeast strains include strains which, optionally, have been cured of endogenous two-micron plasmids and/or which optionally lack yeast peptidase activity(ies), e.g. peptidase ysc$\alpha$, yscA, yscB, yscY and/or yscS activity.

The yeast strains of the invention are used for the preparation of a hybrid protein of the invention.

The transformation of yeast with the hybrid (rectors according to the invention is accomplished by methods known in the art, for example according to the methods described by Hinnen et al. (Proc. Natl. Acad. Sci. USA (1978) 75, 1929) and Ito et at. (J. Bact. (1983) 153, 163–168).

The transformed yeast strains are cultured using methods known in the art.

Thus, the transformed yeast strains according to the invention are cultured in a liquid medium containing assimilable sources of carbon, nitrogen and inorganic salts.

Various carbon sources are usable. Examples of preferred carbon sources are assimilable carbohydrates, such as glucose, maltose, mannitol, fructose or lactose, or an acetate such as sodium acetate, which can be used either alone or in suitable mixtures. Suitable nitrogen sources include, for example, amino acids, such as casamino acids, peptides and proteins and their degradation products, such as tryptone, peptone or meat extracts, furthermore yeast extract, malt extract, corn steep liquor, as well as ammonium salts, such as ammonium chloride, sulphate or nitrate which can be used either alone or in suitable mixtures. Inorganic salts which may be used include, for example, sulphates, chlorides, phosphates and carbonates of sodium, potassium, magnesium and calcium. Additionally, the nutrient medium may also contain growth promoting substances. Substances which promote growth include, for example, trace elements, such as iron, zinc, manganese and the like, or individual amino acids.

Due to the incompatibility between the endogenous two-micron DNA and hybrid vectors carrying its replicon, yeast cells transformed with such hybrid vectors tend to lose the latter. Such yeast cells have to be grown under selective conditions, i.e. conditions which require the expression of a plasmid-encoded gene for growth. Most selective markers currently in use and present in the hybrid vectors according to the invention (infra) are genes coding for enzymes of amino acid or purine biosynthesis. This makes it necessary to use synthetic minimal media deficient in the corresponding amino acid or purine base. However, genes conferring resistance to an appropriate biocide may be used as well [e.g. a gene conferring resistance to the amino-glycoside G418]. Yeast cells transformed with vectors containing antibiotic resistance genes are grown in complex media containing the corresponding antibiotic whereby faster growth rates and higher cell densities are reached.

Hybrid vectors comprising the complete two-micron DNA (including a functional origin of replication) are stably maintained within strains of *Saccharomyces cerevisiae* which are devoid of endogenous two-micron plasmids (so-called cir° strains) so that the cultivation can be carried out under non-selective growth conditions, i.e. in a complex medium.

Yeast cells containing hybrid plasmids with a constitutive promoter express the DNA encoding a glycosyltransferase, or a variant thereof, controlled by said promoter without induction. However, if said DNA is under the control of a regulated promoter the composition of the growth medium has to be adapted in order to obtain maximum levels of mRNA transcripts, e.g. when using the PH05 promoter the growth medium must contain a low concentration of inorganic phosphate for derepression of this promoter.

The cultivation is carried out by employing conventional techniques. The culturing conditions, such as temperature, pH of the medium and fermentation time are selected in such a way that maximal levels of the heterologous protein are produced. A chosen yeast strain is e.g. grown under aerobic conditions in submerged culture with shaking or stirring at a temperature of about 25° to 35° C., preferably at about 28° C., at a pH value of from 4 to 7, for example at approximately pH 5, and for at least 1 to 3 days, preferably as long as satisfactory yields of protein are obtained.

After expression in yeast the hybrid protein of the invention is either accumulated inside the cells or secreted by the cells. In the latter case the hybrid protein is found within the periplasmic space and/or in the culture medium. The enzymatic activity may be recovered e.g. by obtaining the protein from the cell or the culture supernatant by conventional means.

For example, the first step usually consists in separating the cells from the culture fluid by centrifugation. In case the hybrid protein has accumulated within the cells, the enzymatic activity is recovered by cell disruption. Yeast cells can be disrupted in various ways well-known in the art: e.g. by exerting mechanical forces such as shaking with glass beads, by ultrasonic vibration, osmotic shock and/or by enzymatic digestion of the cell wall. If desired, the crude extracts thus obtainable can be directly used for glycosylation. Further enrichment may be achieved for example by differential centrifugation of the cell extracts and/or treatment with a detergent, such as Triton.

In case the hybrid protein is secreted by the yeast cell into the periplasmic space, a simplified isolation protocol can be used: the protein is isolated without cell lysis by enzymatic removal of the cell wall or by chemical agents, e.g. thiol reagents or EDTA, which gives rise to cell wall damages permitting the produced hybrid protein to be released. In case the hybrid protein of the invention is secreted into the culture broth, the enzymatic activity can be isolated directly therefrom.

Methods suitable for the purification of the crude hybrid protein include standard chromatographic procedures such as affinity chromatography, for example with a suitable substrate, antibodies or Concanavalin A, ion exchange chromatography, gel filtration, partition chromatography, HPLC, electrophoresis, precipitation steps such as ammonium sulfate precipitation and other processes, especially those known from the literature.

In order to detect glycosyltransferase activity assays known from the literature can be used. For example, galactosyltransferase activity can be measured by determining the mount of radioactively labelled galactose incorporated into a suitable acceptor molecule such as a glycoprotein or a free sugar residue. Analogously, sialyltransferase activity may be assayed e.g. by the incorporation of sialic acid into a suitable substrate. For a hybrid protein exhibiting two different glycosyltransferase activities the activities may be assessed individually or together in a 'single pot assay'.

A hybrid protein of the invention is useful e.g. for the synthesis or modification of glycoproteins, oligosaccharides and glycolipids. If the hybrid molecule comprises two different glycosyltransferase activities glycosylation in a one pot reaction is preferred.

The invention especially concerns the hybrid proteins, the recominant DNA molecules coding therefor, the hybrid vectors and the transformed yeast strains, and the processes for the preparation thereof, as described in the Examples.

In the Examples, the following abbreviations are used: GT=galactosyltransferase (EC 2.4.1.22), PCR=polymerase chain reaction; ST=sialyltransferase (EC 2.4.99.1).

dithiothreitol, 1 µl mixed dNTP (10 mM each dATP, dCTP, dGTP, dTTP, Pharmacia), 0.5 µl (17.5 U) RNAguard (RNase Inhibitor of Pharmacia) and 1 µl (200 U)M-MLVH-RT are added. The reaction is carried out at 42° C. and stopped after 1 h by heating the robe to 95° C. for 10 min.

In order to check the efficiency of the reaction an aliquot of the mixture (5 µl) is incubated in the presence of 2 µCi $\alpha$-$^{32}$P dCTP. By measuring the incorporated dCTP, the amount of cDNA synthesized is calculated. The yield of first strand synthesis is routinely between 5 and 15 %.

1.3 Polymerase chain reaction

The oligodeoxynucleotide primers used for PCR are synthesized in vitro by the phosphoramidite method (M. H. Caruthers, in Chemical and Enzymatic Synthesis of Gene Fragments, H. G. Gassen and A. Lang, eds., Verlag Chemie, Weinheim, FRG) on an Applied Biosystems Model 380B synthesizer. They are listed in Table 1.

TABLE 1

PCR-primers

| primer | | sequence (5' to 3')[1] | corresponding to bp in GT cDNA[2] |
|---|---|---|---|
| P1up | (KpnI) | cgcggtACCCTTCTTAAAGCGGCGGCGGGAAGATG | (−26)−3 |
| P1 | (EcoRI) | gccgaattcATGAGGCTTCGGGAGCCGCTCCTGAGCG | 1−28 |
| P3 | (SacI) | CTGGAGCTCGTGGCAAAGCAGAACCC | 448−473 |
| P2d | (EcoRI) | gccgaaTTCAGTCTTTACCTGTACCAAAAGTCCTA | 1222−1192 |
| P4 | (HindIII) | cccaagctTGGAATGATGATGGCCACCTTGTGAGG | 546−520 |

[1] Capital letters represent sequences from GT, small letters are additional sequences, sites for restriction enzymes are underlined. Codons for 'start' and 'stop' of RNA translation are highlighted in boldface.
[2] GT cDNA sequence from human placenta published in GenBank (Accession No. M22921).

EXAMPLE 1

Cloning of the galactosyltransferase (GT) cDNA from HeLa cells

GT cDNA is isolated from HeLa cells (Watzele, G. and Berger, E.G. (1990) Nucleic Acids Res. 18, 7174) by the polymerase chain reaction (PCR) method:

1.1 Preparation of poly(A)$^+$RNA from HeLa cells

For RNA preparation HeLa cells are grown in monolayer culture on 5 plates (23×23 cm). The rapid and efficient isolation of RNA from cultured cells is performed by extraction with guanidine-HCl as described by Mac Donald, R. J. et al (Meth. Enzymol. (1987) 152, 226–227). Generally, yields are about 0.6–1 mg total RNA per plate of confluent cells. Enrichment of poly(A)$^+$RNA is achieved by affinity chromatography on oligo(dT)-cellulose according to the method described in the Maniatis manual (Sambrook, J., Fritsch, E. F. and Maniatis, T. (1989) Molecular Cloning: A Laboratory Manual (2nd edition), Cold Spring Harbor Laboratory Press, Cold Spring Habor, USA), applying 4 mg of total RNA on a 400 µl column. 3 % of the loaded RNA are recovered as enriched poly(A)$^+$RNA which is stored in aliquots precipitated with 3 volumes of ethanol at −70° C. until it is used.

1.2 First strand cDNA synthesis for PCR

Poly(A)$^+$RNA (mRNA) is reverse-transcribed into DNA by Moloney Murine Leukemia Virus RNase H-Reverse Transcriptase (M-MLV H-RT) (BRL). In setting up the 20 µl reaction mix, the protocol provided by BRL is followed with minor variations: 1 µg of HeLa cell poly(A)$^+$RNA and 500 ng Oligo(dT)$_{12-18}$ (Pharmacia) in 11.5 µl sterile H$_2$O are heated to 70° C. for 10 min and then quickly chilled on ice. Then 4 µl reaction buffer provided by BRL (250 mM Tris-HCl pH 8.3, 375 mM KCl, 15 mM MgCl2), 2 µl 0.1M Standard PCR-conditions for a 30 µl incubation mixture are: 1 µl of the Reverse Transcriptase reaction (see Example 1.2), containing about 5 ng first strand cDNA, 15 pmol each of the relevant primers, 200 µmol each of the four deoxynucleoside triphosphates (dATP, dCTP, dGTP and dTTP) in PCR-buffer (10 mM Tris-HCl pH 8.3 (at 23° C.), 50 mM KCl, 1.5 mM MgCl$_2$, 0.001% gelatine) and 0.5 U AmpliTaq Polymerase (Perkin Elmer). The amplification is performed in the Thermocycler 60 (Biomed) using the following conditions: 0.5 min denaturing at 95° C., 1 min annealing at 56° C., and 1 min 15 sec extension at 72° C., for a total of 20–25 cycles. In the last cycle, primer extension at 72° C. is carried out for 5 min.

For sequencing and subcloning, the HeLa GT cDNA is amplified in two overlapping pieces, using different primer combinations:

(1) Fragment P1-P4: Primers P1 and P4 are used to amplify a DNA fragment covering nucleotide positions 7–555 in the nucleotide sequence depicted in SEQ ID NO. 1.

(2) Fragment P3- P2d: Primers P3 and P2d are used to amplify a DNA fragment covering nucleotide positions 457–1229 in the nucleotide sequence depicted in SEQ ID NO. 1.

In order to avoid errors during amplification four independent PCRs are carried out for each fragment. Also primer P1up (KpnI) in combination with palmer P4 is used to determine the DNA sequence followed by the 'start' codon.

After PCR amplification, fragment P1- P4 is digested with the restriction enzymes EcoRI and HindIII, analysed on a 1.2% agarose gel, eluted from the gel by GENECLEAN (BIO 101) and subcloned into the vector pUC18 (Pharmacia), digested with the same enzymes. Fragment P3-

P2d is digested with SacI and EcoRI, analysed on a 1.2% gel, eluted and subcloned into pUC18, digested with SacI and EcoRI. The resulting subclones are pUC18/P1- P4 and pUC18/P3- P2d, respectively. For subcloning, ligation and transformation of *E. coli* strain DH5α, standard protocols are followed as described in Example 2. Minipreparations of Plasmids pUC18/P1- P4 and pUC 18/P3- P2d are used for dideoxy-sequencing of denatured double-stranded DNA with the T7 polymerase Sequencing kit (Pharmacia). M13/pUC sequencing primers and reverse sequencing primers (Pharmacia) are applied to sequence overlapping fragments produced from both DNA strands by digestion with various restriction enzymes. Further subcloning of restriction fragments of the GT gene is necessary for extensive sequencing of overlapping fragments of both strands. The sequence of fragments amplified by independent PCRs shows that the error of amplification is less than 1 in 3000 nucleotides. The complete nucleotide sequence of the HeLa cell GT cDNA which is presented in SEQ ID NO. 1 is 99.2% homologous to that of human placenta (Genbank Accession No. M22921). Three differences are found:

(a) Three extra base pairs at nucleotide positions 37–39 (SEQ ID NO. 1) resulting in one extra amino acid (Ser) in the N-terminal region of the protein; (b) bp 98 to 101 are 'CTCT' instead of 'TCTG' in the sequence of human placenta, leading to two conservative amino acid substitutions (Ala Leu instead of ValTyr) at amino acid positions 31 and 32 in the membrane spanning domain of GT; (c) the nucleotide at position 1047 is changed from 'A' to 'G' without ensuing a change in amino acid sequence.

The two overlapping DNA-fragments P1- P4 and P3- P2d encoding the HeLa GT cDNA are joined via the NotI restriction site at nucleotide position 498 which is present in both fragments.

The complete HeLa cell GT cDNA is cloned as a 1.2 kb EcoRI-EcoRI restriction fragment in plasmid pIC-7, a derivative of pUC8 with additional restriction sites in the multicloning site (Marsh, J. L., Erfle, M. and Wykes, E. J. (1984) Gene 32, 481–485), resulting in vector p4AD113. SEQ ID NO. 1 shows the DNA sequence of the EcoRI-HindIII fragment from plasmid p4AD113 comprising HeLa cell cDNA coding for full-length GT (EC 2.4.1.22), said fragment having the following features:

| | |
|---|---|
| from 6 to 1200 bp | cDNA sequence coding for HeLa cell galactosyltransferase |
| from 1 to 6 bp | EcoRI site |
| from 497 to 504 bp | NotI site |
| from 1227 to 1232 bp | EcoRI site |
| from 1236 to 1241 bp | EcoRV site |
| from 1243 to 1248 bp | BglII site |

For the purpose of creating the GT expression cassette the EcoRI restriction site (bp 1227) at the 3' end of the cDNA sequence is deleted as follows: vector p4AD113 is first linearized by digestion with EcoRV and then treated with alkaline phosphatase. Furthermore, 1 µg of the linearised plasmid DNA is partially digested with 0.25 U EcoRI for 1 h at 37° C. After agarose gel electrophoresis a fragment corresponding to the size of the linearized plasmid (3.95 kb) is isolated from the gel by GENECLEAN (Bio 101). The protruding EcoRI end is filled in with Klenow polymerase as described in the Maniatis manual (supra). After phenolisation and ethanol precipitation the plasmid is religated and used to transform *E. coli* DH5α(Gibco/BRL). Minipreparation of plasmids are prepared from six transformants. The plasmids obtained are checked by restriction analysis for the absence of the EcoRI and EcoRV restriction sites at the 3' end of HeLa GT cDNA. The plasmid designated p4AE113 is chosen for the following experiments, its DNA sequence being identical to that of plasmid p4AD113, with the exception that bp 1232–1238 with the EcoRI-EcoRV restriction sites are deleted.

EXAMPLE 2

Construction of expression cassettes for full length GT

For heterologous expression in *Saccharomyces cerevisiae* the full length HeLa GT cDNA sequence (SEQ ID NO. 1) is fused to transcriptional control signals of yeast for efficient initiation and termination of transcription. The promoter and terminator sequences originate from the yeast acid phosphatase gene (PH05) (EP 100561). A short, 173 bp PH05 promoter fragment is used, which is devoid of all regulatory elements and therefore behaves as a constitutive promoter.

The GT cDNA sequence is combined with a yeast 5' truncated PH05 promoter fragment and transcription terminator sequences as follows:

(a) Full length HeLa GT cDNA sequence:

Vector p4AE113 with the full length GT cDNA sequence is digested with the restriction enzymes EcoRI and BglII. The DNA fragments are electrophoretically separated on a 1% agarose gel. A 1.2 kb DNA fragment containing the complete cDNA sequence for HeLa GT is isolated from the gel by adsorption to glasmilk, using the GENECLEAN kit (BIO 101). On this fragment the 'ATG' start codon for protein synthesis of GT is located directly behind the restriction site for EcoRI whereas the stop codon 'TAG' is followed by 32 bp contributed by the 3' untranslated region of HeLa GT and the multiple cloning site of the vector with the BglII restriction site.

(b) Vector for amplification in *E. coli*:

The vector for amplification, plasmid p31R (cf. EP 100561), a derivative of pBR322, is digested with the restriction enzymes BamHI and SalI. The restriction fragments are separated on a 1% agarose gel and a 3.5 kb vector fragment is isolated from the gel as described before. This DNA fragment contains the large SalI-HindIII vector fragment of the pBR322 derivative as well as a 337 bp PH05 transcription terminator sequence in place of the HindIII-BamHI sequence of pBR322.

(c) Construction of plasmid p31/PH05(-173)RIT

The 5' truncated PH05 promoter fragment without phosphate regulatory elements is isolated from plasmid p31/PH05(-173)RIT.

Plasmid p31 RIT12 (EP 288435) comprises the full length, regulated PH05 promoter (with an EcoRI site introduced at nucleotide position-8 on a 534bp BamHI-EcoRI fragment, followed by the coding sequence for the yeast invertase signal sequence (72bp EcoRI-XhoI) and the PH05 transcription termination signal (135 bp XhoI-HindIII) cloned in a tandem array between BamHI and HindIII of the pBR322 derived vector.

The constitutive PH05(-173) promoter element from plasmid pJDB207/PH05(-173)-YHIR (EP 340170) comprises the nucleotide sequence of the yeast PH05 promoter from nucleotide position-9 to -173 (BstEII restriction site), but has no upstream regulatory sequences (UASp). The PH05 (-173) promoter, therefore, behaves like a constitutive promoter. The regulated PH05 promoter in plasmid p31RIT12 is replaced by the short, constitutive PH05 (-173) promoter element in order to obtain plasmid p31/PH05 (-173) RIT.

Plasmids p31RIT12 (EP 288435) and pJDB207/PHO5(-173)-YHIR (EP 340170) are digested with restriction endonucleases SalI and EcoRI. The respective 3.6 kb and 0.4 kb SalI-EcoRI fragments are isolated on a 0.8% agarose gel, eluted from the gel, ethanol precipitated and resuspended in $H_2O$ at a concentration of 0.1 pmoles/µl. Both DNA fragments are ligated and 1 µl aliquots of the ligation mix are used to transform E. coli HB 101 (ATCC) competent cells. Ampicillin resistant colonies are grown individually in LB medium supplemented with ampicillin (100 µg/ml). Plasmid DNA is isolated according to the method of Holmes, D. S. et al. (Anal. Biochem. (1981) 144, 193) and analysed by restriction digests with SalI and EcoRI. The plasmid of one clone with the correct restriction fragments is referred to as p31/PHO5(-173)RIT.

(d) Construction of plasmid pGTB 1135

Plasmid p31/PHO5(-173)RIT is digested with the restriction enzymes EcoRI and SalI. After separation on a 1% agarose gel, a 0.45 kb SalI-EcoRI fragment (fragment (c)) is isolated from the gel by GENECLEAN (BIO 101). This fragment contains the 276 bp SalI-BamHI sequence of pBR322 and the 173 bp BamHI(BstEII)-EcoRI constitutive PHO5 promoter fragment. The 0.45 kb SalI-EcoRI fragment is ligated to the 1.2 kb EcoRI-BglII GT cDNA (fragment (a)) and the 3.5 kb BamHI-SalI vector part for amplification in E. coli with the PHO5 terminator (fragment (b)) described above.

The three DNA fragments (a) to (c) are ligated in a 12 µl ligation mixture: 100 ng of DNA fragment (a) and 30 ng each of fragments (b) and (c) are ligated using 0.3 U T4 DNA ligase (Boehringer) in the supplied ligase buffer (66 mM Tris-HCl pH 7.5, 1 mM dithioerythritol, 5 mM $MgCl_2$, 1 mM ATP) at 15° C. for 18 hours. Half of the ligation mix is used to transform competent cells of E. coli strain DH5α (Gibco/BRL). For preparing competent cells and for transformation, the standard protocol as given in the Maniatis manual (supra) is followed. The cells are plated on selective LB-medium, supplemented with 75 µg/ml ampicillin and incubated at 37° C. 58 transformants are obtained. Minipreparations of plasmid are performed from six independent transformants by using the modified alkaline lysis protocol of Birnboim, H. C. and Doly, J. as described in the Maniatis manual (supra). The isolated plasmids are characterized by restriction analysis with four different enzymes (EcoRI, PstI, HindIII, SalI, also in combination). All six plasmids show the expected fragments. One correct clone is referred to as pGTB 1135. Plasmid pGTB 1135 contains the expression cassette with the full-lenght HeLaGT cDNA under the control of the constitutive PHO5 (-173) promoter fragment, and the PHO5 transcriptional terminator sequence. This expression cassette can be excised from vector pGTB 1135 as a 2 kb SalI-HindIII fragment.

EXAMPLE 3

Construction of plasmids pA1 and pA2

3.1 PCR for site-directed mutagenesis

In order to knock out the stop codon of the GT coding sequence and to allow for an in frame fusion with ST a frame shift mutation and a point mutation are introduced into the cDNA coding for HeLa GT. The oligonucleotide primers used for PCR are synthesized in vitro according to the phosphoramidite method (supra) and listed in Table 2.

TABLE 2

| primer | | sequence (5' to 3')[1] | corresponding to bp in SEQ ID NO. 3 |
|---|---|---|---|
| P3 | (SacI) | CTGGAGCTCGTGGCAAAGCAGAACCC | 457–482 |
| P2A1 | (BamHI) | ggggaTCCTAGCTCG-TGTCCC | 1205–1189 |
| P2B1 | (BamHI) | ggggaTCCCAGCTCG-TGTCCC | 1205–1189 |

[1] Capital letters represent sequences from GT, small letters are additional sequences, sites for restriction enzymes are underlined. Codons for 'start' and 'stop' of RNA translation are highlighted in boldface.

Standard PCR-conditions for a 30 µl incubation mixture are: 1 µl of the Reverse Transcriptase reaction mix containing about 5 ng first strand cDNA (see Example 1.2), 15 pmol each of the relevant primers, 200 µmol each of the four deoxynucleoside triphosphates (dATP, dCTP, dGTP and dTTP) in PCR-buffer (10 mM Tris-HCl pH 8.3 (at 23° C.), 50 mM KCl, 1.5 mM $MgCl_2$, 0.001% gelatine) and 0.5 U AmpliTaq Polymerase (Perkin Elmer). The amplification is performed in the Thermocycler 60 (Biomed) using the following conditions: 0.5 min denaturing at 95° C., 1 min annealing at 56° C., and 1 min 15 sec extension at 72° C., for a total of 20–25 cycles. In the last cycle, primer extension at 72° C. is carried out for 5 min.

For sequencing and subcloning, the HeLa GT cDNA is amplified as described above, yielding "mutated" fragments:

(3) Fragment P3-P2A1: primers P3 and P2A1 are used to amplify a 0.77 kb fragment covering nucleotides 457–1205 in the sequence depicted in SEQ ID NO. 3

(4) Fragment P3-P2B 1: primers P3 and P2B 1 are used to amplify a 0.77 kb fragment covering nucleotide positions 457–1205 in the sequence depicted in SEQ ID NO. 3.

3.2 Construction of plasmids pA1 and pA2

Fragments P3-P2A1 and P3-P2B 1, respectively, are amplified by PCR, digested with BamHI1 and SacI and subcloned into vector pUC18 (Pharmacia), digested with the same enzyme to produce plasmids pA1 and pA2.

EXAMPLE 4

Cloning of the sialyltransferase (ST) cDNA from human HepG2 cells

ST cDNA is isolated from HepG2 cells by PCR in analogy to GT cDNA. Preparation of poly (A)⁻RNA and first strand cDNA synthesis are performed as described in Example 1. The primers (Microsynth) listed in Table 3 are used for PCR.

TABLE 3

PCR-primers

| primer | sequence (5' to 3')[1] | corresponding to bp in ST cDNA[2] |
|---|---|---|
| SIA1 | PstI/EcoRI<br>cgctgcagaattcaaaATGATTCACACCAACCTGAAGAAAAAGT | 1–28 |
| SIA3 | BamHI<br>cgcggatCCTGTGCTTAGCAGTGAATGGTCCGGAAGCC | 1218–1198 |

[1] Capital letters represent sequences from ST, small letters are additional sequences with sites for restriction enzymes (underlined). Codons for 'start' and 'stop' for protein synthesis are indicated in boldface.
[2] ST cDNA sequence from human placenta as published in EMBL Data Bank (Accession No. X17247)

HepG2 ST cDNA can be amplified as one DNA fragment of 1.2 kb using the primers SIA1 and SIA3. PCR is performed as described for GT cDNA under slightly modified cycling conditions: 0.5 min denaturing at 95° C., 1 min. 15 sec annealing at 56° C., and 1 min 30 sec extension at 72° C., for a total of 25–35 cycles. In the last cycle, primer extension at 72° C. is carried out for 5 min.

After PCR amplification, the 1.2 kb fragment is digested with the restriction enzymes BamHI and PstI, analysed on a 1.2% agarose gel, eluted from the gel and subcloned into the vector pUC18. The resulting subclone is designated pSIA2. The nucleotide sequence of the PstI-BamHI fragment from plasmid pSIA2 comprising HepG2 cDNA coding for full-length sialyltransferase is presented in SEQ ID NO. 3, said fragment having the following features:

| from 15 to 1232 bp | cDNA sequence coding for HepG2 cell sialyltransferase |
|---|---|
| from 1 to 6 bp | PstI site |
| from 6 to 11 bp | EcoRI site |
| from 144 to 149 bp | EcoRI site |
| from 1241 to 1246 bp | BamHI site. |

EXAMPLE 5

Construction of plasmids pA1ST and pB1ST a) Plasmid pSIA2 is double digested using EcoR1/BamH1 and the ensuing 1098 bp fragment (fragment (a)) is isolated. The fragment codes for a soluble ST designated $ST_{(44-406)}$ starting at amino acid position 44 (Glu) and extending to amino acid position 406 (Cys) (SEQ ID NO. 4).

b) Plasmids A1 and B1 are linearized by BamH1 digestion, treated with alkaline phosphatase and separated from contaminating enzymes by gel electrophoresis using GENECLEAN (Bio 101).

c) Fragment (a) is linked to fragment (b) by means of an adaptor sequence from equimolar mounts of the synthesized oligonucleotides (Microsynth):

5' GATCCGTCGACCTGCAG 3' and 5' AATTCAG-CAGGTCGACG 3' for the complementary strand. The oligonucleotides are annealed to each other by first heating to 95° C. and then slowly cooling to 20° C. Ligation is carried out in 12 μl of ligase buffer (66 mM Tris-HCl pH 7.5, 1 mM dithioerythritol, 5 mM MgCl₂, 1 mM ATP) at 16° C. for 18 hours. The sequences at the junction of GT and ST are as follows:

```
pA1ST:                 BamH1 Adaptor  (bold)    EcoR1
GGG ACA CGA GCT AGG ATC CGT CGA CCT GCA GAA TTC CAG GTG
Gly Thr Arg Ala Arg Ile Arg Arg Pro Ala Glu Phe Gln Val pB1ST:
GGG ACA CGA GCT GGG ATC CGT CGA CCT GCA GAA TTC CAG GTG
Gly Thr Arg Ala Gly Ile Arg Arg Pro Ala Glu Phe Gln Val
```

The ligated plasmids pA1 ST and pB 1 ST are transformed into E. coli strain DH5α. Plasmid DNA of 6 transformants from each transformation is isolated and digested with EcoRI to test the orientation of the BamHI insert. Plasmids with a 3900 bp together with a 700 bp EcoRI fragment are used for the next step.

EXAMPLE 6

Construction of the GT-ST expression vectors YEPGSTa and YEPGSTb 6.1 Isolation of a NotI-BamHI fragment coding for the GT C-terminus fused to ST Plasmids pA1ST and pB1ST are linearised by cutting with NotI and then partially digested with BamHI. After gel electrophoresis a 1900 bp NotI-BamHI fragment coding for the GT C-terminus fused to ST is isolated.

6.2 Construction of the YEPGTB vector

The episomal yeast vector YEP352 (S. E. Hill et al., Yeast 2, 163–167, 1986) is used to construct the YEPGTB vector which contains the constitutive PHO5 promoter, the cDNA coding for full length GT and the PHO5 transcriptional terminator sequence. YEP352 is digested with the restriction enzymes SalI and HindIII at the multiple cloning site. After separation over an 0.8% agarose gel the linearized vector is isolated as a 5.2 kb DNA fragment (vector part) from the gel with the GENECLEAN kit (Bio 101). Vector pGTB 1135 (Example 2) is also digested with the restriction enzymes SalI and HindIII. A 2.0 kb fragment containing the expression cassette with the constitutive promoter is isolated. Ligation of the yeast vector and the exprssion cassette is carried out as follows: in a 12 μl ligation mix, 80 ng of the vector part (5.2 kb fragment) is combined with 40 ng of the 2.0 kb SalI-HindIII fragment using 0.3 U ligase (Boehringer) in the supplied buffer (66 mM Tris-HCl pH 7.5, 1 mM dithioerythritol, 5 mM MgCl₂, 1 mM ATP) for 18 hours at 15° C. The ligation mix is used to transform E. coli DH5α as described above. 24 transformants are obtained.

Four independent colonies are chosen for minipreparation of plasmids. The isolated plasmids are characterized by restriction analysis: all four analyzed plasmids (YEPGTB 21–24) show the expected restriction patterns. YEPGTB24 is used for further experiments.

6.3 Isolation of the fragment coding for the N-terminal part of GT.

YEPGTB24 carrying the whole constitutive expression cassette for GT in the yeast-E.coli shuttle vector YEP352 is cut with NotI and HindIII and a 6.3 kb fragment is isolated after gel electrophoresis.

6.4 PHO5-terminator sequence

Plasmid p31 RIT12 (EP 288435) is cut with BamHI and HindIII and a 400 bp fragment carrying the PHO5 terminator sequnce is isolated.

Fragments isolated as described in 6.1 (1.9 kb NotI-BamHI fragment, 6.3 (6.3 kb HindIII -NotI fragment) and 6.4 (0.4 kb BamHI-HindIII fragment) are ligated to yield plasmids YEPGSTa and YEPGSTb, respectively, which are transformed in the E.coli strain DH5α. Plasmid DNA of transformants carrying the predicted pattern of BamHI fragments with 5580 bp, 1375 bp, 1150 bp and 276 bp are used for yeast transformation. The nucleotide sequences of the cDNAs coding for the hybrid glycosyltransferases designated GT-STa and GT-STb are presented in SEQ ID NOs. 5 and 7, respectively, said sequences having the following common features:

| from 1 to 1188 bp | cDNA sequence coding for HeLa cell $GT_{(1-396)}$ (cf. SEQ ID NO. 1) |
|---|---|
| from 1189 to 1212 bp | Adaptor |
| from 1213 to 2301 bp | cDNA sequence coding for HepG2cell $ST_{(44-406)}$ |

EXAMPLE 7

Transformation of yeast strain BT 150

CsCl-purified DNA of the expression vectors YEPGSTa and YEPGSTb is prepared following the protocol of R. Treisman in the Maniatis manual (supra). The protease deficient S. cerevisiae strain BT 150 (MATα, his4, leu2, ura3, pra1, prb1, prc1, cps1) is transformed with about 1 µg of plasmids YEPGSTa and YEPGSTb, respectively, according to the lithium-acetate transformation method (Ito et al., J. Bact. (1983) 153, 163–168). Approximately 200 transformants are obtained with YEPGSTa and YEPGSTb on SD plates (0.67% yeast nitrogen base without amino acids, 2% glucose, 2% agarose supplemented with leucine (30 µg/ml) and histidine (20 µg/ml). Single transformed yeast cells are selected and referred to as Saccharomyces cerevisiae BT 150/YEPGSTa and Saccharomyces cerevisiae BT 150/YEPGSTb, respectively.

EXAMPLE 8

Enzyme activity of the GT-ST hybrid proteins 8.1 Preparation of cell extracts

Preparation of cell extracts

Cells of transformed Saccharomyces cerevisiae strains BT 150 are each grown under uracil selection in yeast minimal media (Difco) supplemented with histidine and leucine. The growth rate of the cells is not affected by the introduction of any of the expression vectors. Exponentially growing cells (at $OD_{587}$ of 2.0) or stationary cells are collected by centrifugation, washed once with 50 mM Tris-HCl buffer pH 7.4 (buffer 1) and resuspended in buffer 1 at a concentration corresponding to 2 $OD_{578}$. A 60 ml culture (120 $OD_{578}$) of yeast cells is washed, pelleted and subjected to mechanical breakage by vigorous shaking on a vortex mixer with glass beads (0.45–0.5 mm diameter) for 4 min with intermittent cooling. The crude extracts are used directly for determination of enzyme activity.

8.2 Protein assay

The protein concentration is determined by use of the BCA-Protein Assay Kit (Pierce).

8.3 Assay for GT activity

GT activity can be measured with radiochemical methods using either ovalbumin, a glycoprotein which solely exposes GlcNAc as acceptor site, or free GlcNAc as acceptor substrates. Cell extracts (of 1–20 $OD_{578}$ of cells) are assayed for 30 min at 37° C. in a 100 µl incubation mixture containing 35 mM Tris-HCl pH 7.4, 25 nCi UDP-$^{14}$C-Gal (1.25 mCi/mmol), 1 µmol $MnCl_2$, 2% Triton X-100 and 1 mg ovalbumin or 20 mM GlcNAc as acceptor substrates. The reaction is terminated by acid precipitation of the protein and the amount of $^{14}$C galactose incorporated into ovalbumin is determined by liquid scintillation counting (Berger, E. G. et al. (1978) Eur. J. Biochem. 90, 213–222). For GlcNAc as acceptor substrate, the reaction is terminated by the addition of 0.4 ml ice cold $H_2O$ and the unused UDP-$^{14}$C-galactose is separated from $^{14}$C products on an anion exchange column (AG X1-8, BioRad) as described (Masibay, A. S. and Qasba, P. K. (1989) Proc. Natl. Acad. Sci. USA 86, 5733–5737). Assays are performed with and without acceptor molecules to assess the extent of hydrolysis of UDP-Gal by nucleotide pyrophosphatases. GT activity is determined in the crude extracts prepared from Saccharomyces cerevisiae BT 150/YEPGSTa and Saccharomyces cerevisiae BT 150/YEPGSTb.

8.4 Determination of optimum detergent activation

The standard assay of GT activity according to Example 8.3 using 10 mM GlcNAc as acceptor substrate is carried out in presence of zero, 0.1, 0.5, 1.0, 2.0, 2.5 and 4% Triton X-100 in the assay. 2% Triton X-100 induce a two fold stimulation as compared with zero % Triton.

8.5 Assay for lactose synthase activity

The assay is carried out and terminated as indicated in Example 8.3 for GlcNAc as acceptor with the following modifications: instead of GlcNAc, 30 mM glucose is used as acceptor. Other ingredients include: 1 mg/ml human α-lactalbumin, 10 mM ATP. Optimum concentration of α-lactalbumin is determined in a range of 0 to 4 mg/ml α-lactalbumin. Maximum lactose synthase activity is observed at 1 mg/ml.

8.6 Assay for ST activity

ST activity can be determined by measuring the amount of radiolabeled sialic acid which is transferred from CMP-sialic acid to a glycoprotein acceptor. In case of the use of a glycoprotein as acceptor such as asialofetuin, the reaction is terminated by acid precipitation using 5% (w/v) phosphotungstic acid and 5% (w/v) trichloroacetic acid. The precipitate is filtered using glass fiber filters (Whatman GFA), washed extensively with ice-cold ethanol and assessed for radioactivity by liquid scintillation counting (Hesford et al. (1984), Glycoconjugate J. 1, 141–153). In case of the use of oligosaccharides as acceptors such as lactose or LacNAc (N-acetyllactosamin), the reaction is terminated by addition of 0.4 ml ice-cold $H_2O$. The unused CMP-$^{14}$C-sialic acid is retained on a 1 ml-column of AG1-X8, phosphate form, 100–200 mesh. The column is washed with 4.5 ml $H_2O$ and eluted with 24 ml 5 mM $K_2HPO_4$ buffer at pH 6.8. Eluant and wash solution are pooled and assessed for radioactivity by liquid scintillation counting. Standard conditions are as follows: 20 µl of yeast extracts (200 to 500 µg protein) are incubated with 300 μg asialofetuin in 2 mM imidazole buffer pH 7.4 and 3 nmoles CMP-$^{14}$sialic acid (specific activity: 2.7 mCi/mmol), Triton X-100 0.5%. ST-activity is found in the crude extracts prepared from Saccharomyces cerevisiae BT 150/YEPGSTa and Saccharomyces cerevisiae BT 150/YEPGSTb.

8.7 Combined GT and ST activity

Yeast extracts prepared from Saccharomyces cerevisiae BT 150/YEPGSTa and Saccharomyces cerevisiae BT 150/YEPGSTb are used to transfer Gal from UDPGal and sialic acid from CMPNeuAc to asialo-agalacto-$\alpha_1$ acid glycoprotein or GlcNAc according to the following conditions: 30 μl of extract, 20 μl of asialo-agalacto-$\alpha_1$ acid glycoprotein (prepared according to Hughes, R. C. and Jeanloz, R. W., (1966), Biochemistry 5, 253–258), 2 mM of unlabeled UDPGal, 60 μM of CMP$^{14}$-sialic acid (specific activity: 5.4 mCi/mmol) in 2 mM imidazole buffer, pH 7.4. ST-activity is shown by incorporation of $^{14}$C-sialic acid. Control incubation carded out in the absence of unlabeled UDPGal results in a 4 times less incorporation of $^{14}$C-sialic acid.

Similar incubations are carried out using 20 mM GlcNAc or 30 mM glucose (in presence of 0.1 mg/ml α-lactalbumin) as acceptor and isolating the product according to 8.6. Linear incorporations of $^{14}$C-sialic acid are observed during 180 min. The assay system contains in a final volume of 1 ml: 3 mmol glucose, 1 mg α-lactalbumin, 1 mM ATP, 1 mmol MnCl$_2$, 20 mmol Tris-HCl, pH 7,4 20 nmol UDPGal, 12 nmol CMP$^{14}$C-sialic acid (4.4 mCi/mmol specific activity) and 350 μg protein (yeast extract). The reaction is terminated by adding 0.4 ml of ice-cold H$_2$O. The mixture is passed over a 2 cm Bio-Rad Poly-Prep® column containing AG1-X8 A6, 100–200 mesh, phosphate form. The column is washed with 4.5 ml H$_2$O and eluted with 24 ml 5 mM K$_2$HPO$_4$ buffer at pH 6.8. 1 ml of the eluant is used for radioactivity measurement by liquid scintillation counting in 10 ml Instagel®.

8.8 Product identification of oligosaccharides synthesized by the GT-ST hybrid proteins 8.8.1 Synthesis of 2,6 sialyllacNAc The incubation mixture contains in a volume of 1.57 ml: 20 mmol GlcNAc, 10 mM ATP, 1 mMol MnCl$_2$, 5 mg Triton X-100, 200 mMol UDPGal, 30 mmol CMP $^{14}$C-sialic acid (4.4 mCi/mmol specific activity) and 1000 μg protein (yeast extract prepared from Saccharomyces cerevisiae BT 150/YEPGSTa and Saccharomyces cerevisiae BT 150/YEPGSTb, respectively). Incubation is carried out for 16 h at 37° C. The reaction is terminated by adding 0.5 ml of H$_2$O. The incubation mixture is separated on AG 1-X8 as described in Example 8.7. The total eluant of the anion exchange column is lyophilized. Then, the residue is dissolved in 0.6 ml H$_2$O followed by separation on a Biogel P2 column (200–400 mesh, 2×90 cm). The column is eluted with H$_2$O at a temperature of 42.5° C. at 5 ml/h. 0.5 ml fractions are collected and assessed for radioactivity in 100 μl aliquots (to which 4 ml Instagel® is added for liquid scintillation counting). The peak fractions containing $^{14}$C are pooled, lyophilized and repurified on AG1-X8 as described in Example 8.7. The total eluant of 24 ml is lyophilized, the resulting residue dissolved in 300 μl H$_2$O. This solution is subjected to preparative thin layer chromatography (Merck Alu plates coated with silicagel 60 F$_{254}$) in a solvent system containing H$_2$O/acetone/n-butanol 2/1.5/1.5 for 5 h and run against authentic standards including 50 mM sialyl 2,6-actose and 2,6 sialyl LacNAc. After drying the products and standards are visualized using a spray containing 0.5 g thymol in 5 ml H$_2$SO$_4$ (96%) and 95 ml ethanol (96%) followed by heating for 10 min at 130° C. The spots detected are found to be at identical positions as the corresponding authentic standards.

---

We claim:

1. A protein having glycosyltransferase activity comprising identical or different catalytically active domains of glycosyltransferases.

2. A protein according to claim 1 which is a hybrid protein.

3. A protein according to claim 2 comprising a membrane-bound or soluble glycosyltransferase linked to a soluble glycosyltransferase.

4. A protein according to claim 2 comprising a suitable linker consisting of genetically encoded amino acids.

5. A protein according to claim 2 selected from the group consisting of the protein having the amino acid sequence depicted in SEQ ID NO. 6 and the protein having the amino acid sequence depicted in SEQ ID NO. 8.

6. A method for preparing a protein according to claim 2 comprising culturing a suitable transformed yeast strain under conditions which allow the expression of said protein.

7. A DNA molecule coding for a protein according to claim 2.

8. A hybrid vector comprising a DNA molecule according to claim 7.

9. A transformed yeast strain comprising a hybrid vector according to claim 8.

* * * * *

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 1265 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( B ) STRAIN: E. coli DH5alpha ( v i i ) IMMEDIATE SOURCE:
        ( B ) CLONE: p4AD113

( i x ) FEATURE:
        ( A ) NAME/KEY: CDS
        ( B ) LOCATION: 7..1200
        ( D ) OTHER INFORMATION: /product="full-length galactosyltransferase"

( x i ) SEQUENCE DESCRIPTION: SEQ ID NO: 1:

```
GAATTC ATG AGG CTT CGG GAG CCG CTC CTG AGC GGC AGC GCC GCG ATG         48
       Met Arg Leu Arg Glu Pro Leu Leu Ser Gly Ser Ala Ala Met
       1               5                   10
```

| | | | | | | | | | | | | | | | | |
|---|---|---|---|---|---|---|---|---|---|---|---|---|---|---|---|---|
| CCA | GGC | GCG | TCC | CTA | CAG | CGG | GCC | TGC | CGC | CTG | CTC | GTG | GCC | GTC | TGC | 96 |
| Pro 15 | Gly | Ala | Ser | Leu | Gln 20 | Arg | Ala | Cys | Arg 25 | Leu | Leu | Val | Ala | Val | Cys 30 | |
| GCT | CTG | CAC | CTT | GGC | GTC | ACC | CTC | GTT | TAC | TAC | CTG | GCT | GGC | CGC | GAC | 144 |
| Ala | Leu | His | Leu | Gly 35 | Val | Thr | Leu | Val | Tyr 40 | Tyr | Leu | Ala | Gly | Arg 45 | Asp | |
| CTG | AGC | CGC | CTG | CCC | CAA | CTG | GTC | GGA | GTC | TCC | ACA | CCG | CTG | CAG | GGC | 192 |
| Leu | Ser | Arg | Leu 50 | Pro | Gln | Leu | Val | Gly 55 | Val | Ser | Thr | Pro | Leu 60 | Gln | Gly | |
| GGC | TCG | AAC | AGT | GCC | GCC | GCC | ATC | GGG | CAG | TCC | TCC | GGG | GAG | CTC | CGG | 240 |
| Gly | Ser | Asn 65 | Ser | Ala | Ala | Ala | Ile 70 | Gly | Gln | Ser | Ser | Gly 75 | Glu | Leu | Arg | |
| ACC | GGA | GGG | GCC | CGG | CCG | CCG | CCT | CCT | CTA | GGC | GCC | TCC | TCC | CAG | CCG | 288 |
| Thr | Gly 80 | Gly | Ala | Arg | Pro | Pro 85 | Pro | Pro | Leu | Gly | Ala 90 | Ser | Ser | Gln | Pro | |
| CGC | CCG | GGT | GGC | GAC | TCC | AGC | CCA | GTC | GTG | GAT | TCT | GGC | CCT | GGC | CCC | 336 |
| Arg 95 | Pro | Gly | Gly | Asp | Ser 100 | Ser | Pro | Val | Val | Asp 105 | Ser | Gly | Pro | Gly | Pro 110 | |
| GCT | AGC | AAC | TTG | ACC | TCG | GTC | CCA | GTG | CCC | CAC | ACC | ACC | GCA | CTG | TCG | 384 |
| Ala | Ser | Asn | Leu | Thr 115 | Ser | Val | Pro | Val | Pro 120 | His | Thr | Thr | Ala | Leu 125 | Ser | |
| CTG | CCC | GCC | TGC | CCT | GAG | GAG | TCC | CCG | CTG | CTT | GTG | GGC | CCC | ATG | CTG | 432 |
| Leu | Pro | Ala | Cys 130 | Pro | Glu | Glu | Ser | Pro 135 | Leu | Leu | Val | Gly | Pro 140 | Met | Leu | |
| ATT | GAG | TTT | AAC | ATG | CCT | GTG | GAC | CTG | GAG | CTC | GTG | GCA | AAG | CAG | AAC | 480 |
| Ile | Glu | Phe 145 | Asn | Met | Pro | Val | Asp 150 | Leu | Glu | Leu | Val | Ala 155 | Lys | Gln | Asn | |
| CCA | AAT | GTG | AAG | ATG | GGC | GGC | CGC | TAT | GCC | CCC | AGG | GAC | TGC | GTC | TCT | 528 |
| Pro | Asn 160 | Val | Lys | Met | Gly | Gly 165 | Arg | Tyr | Ala | Pro | Arg 170 | Asp | Cys | Val | Ser | |
| CCT | CAC | AAG | GTG | GCC | ATC | ATC | ATT | CCA | TTC | CGC | AAC | CGG | CAG | GAG | CAC | 576 |
| Pro 175 | His | Lys | Val | Ala | Ile 180 | Ile | Ile | Pro | Phe | Arg 185 | Asn | Arg | Gln | Glu | His 190 | |
| CTC | AAG | TAC | TGG | CTA | TAT | TAT | TTG | CAC | CCA | GTC | CTG | CAG | CGC | CAG | CAG | 624 |
| Leu | Lys | Tyr | Trp | Leu 195 | Tyr | Tyr | Leu | His | Pro 200 | Val | Leu | Gln | Arg | Gln 205 | Gln | |
| CTG | GAC | TAT | GGC | ATC | TAT | GTT | ATC | AAC | CAG | GCG | GGA | GAC | ACT | ATA | TTC | 672 |
| Leu | Asp | Tyr | Gly 210 | Ile | Tyr | Val | Ile | Asn 215 | Gln | Ala | Gly | Asp | Thr 220 | Ile | Phe | |
| AAT | CGT | GCT | AAG | CTC | CTC | AAT | GTT | GGC | TTT | CAA | GAA | GCC | TTG | AAG | GAC | 720 |
| Asn | Arg | Ala | Lys 225 | Leu | Leu | Asn | Val | Gly 230 | Phe | Gln | Glu | Ala | Leu 235 | Lys | Asp | |
| TAT | GAC | TAC | ACC | TGC | TTT | GTG | TTT | AGT | GAC | GTG | GAC | CTC | ATT | CCA | ATG | 768 |
| Tyr | Asp 240 | Tyr | Thr | Cys | Phe | Val 245 | Phe | Ser | Asp | Val | Asp 250 | Leu | Ile | Pro | Met | |
| AAT | GAC | CAT | AAT | GCG | TAC | AGG | TGT | TTT | TCA | CAG | CCA | CGG | CAC | ATT | TCC | 816 |
| Asn 255 | Asp | His | Asn | Ala | Tyr 260 | Arg | Cys | Phe | Ser | Gln 265 | Pro | Arg | His | Ile | Ser 270 | |
| GTT | GCA | ATG | GAT | AAG | TTT | GGA | TTC | AGC | CTA | CCT | TAT | GTT | CAG | TAT | TTT | 864 |
| Val | Ala | Met | Asp | Lys 275 | Phe | Gly | Phe | Ser | Leu 280 | Pro | Tyr | Val | Gln | Tyr 285 | Phe | |
| GGA | GGT | GTC | TCT | GCT | CTA | AGT | AAA | CAA | CAG | TTT | CTA | ACC | ATC | AAT | GGA | 912 |
| Gly | Gly | Val | Ser 290 | Ala | Leu | Ser | Lys | Gln 295 | Gln | Phe | Leu | Thr | Ile 300 | Asn | Gly | |
| TTT | CCT | AAT | AAT | TAT | TGG | GGC | TGG | GGA | GGA | GAA | GAT | GAT | GAC | ATT | TTT | 960 |
| Phe | Pro | Asn 305 | Asn | Tyr | Trp | Gly | Trp 310 | Gly | Gly | Glu | Asp | Asp 315 | Asp | Ile | Phe | |
| AAC | AGA | TTA | GTT | TTT | AGA | GGC | ATG | TCT | ATA | TCT | CGC | CCA | AAT | GCT | GTG | 1008 |
| Asn | Arg | Leu 320 | Val | Phe | Arg | Gly | Met 325 | Ser | Ile | Ser | Arg | Pro 330 | Asn | Ala | Val | |

5,641,668

-continued

| | | | | | | | | | | | | | | | | |
|---|---|---|---|---|---|---|---|---|---|---|---|---|---|---|---|---|
| GTC | GGG | AGG | TGT | CGC | ATG | ATC | CGC | CAC | TCA | AGA | GAC | AAG | AAA | AAT | GAA | 1056 |
| Val | Gly | Arg | Cys | Arg | Met | Ile | Arg | His | Ser | Arg | Asp | Lys | Lys | Asn | Glu | |
| 335 | | | | 340 | | | | | 345 | | | | | 350 | | |
| CCC | AAT | CCT | CAG | AGG | TTT | GAC | CGA | ATT | GCA | CAC | ACA | AAG | GAG | ACA | ATG | 1104 |
| Pro | Asn | Pro | Gln | Arg | Phe | Asp | Arg | Ile | Ala | His | Thr | Lys | Glu | Thr | Met | |
| | | | | 355 | | | | | 360 | | | | | 365 | | |
| CTC | TCT | GAT | GGT | TTG | AAC | TCA | CTC | ACC | TAC | CAG | GTG | CTG | GAT | GTA | CAG | 1152 |
| Leu | Ser | Asp | Gly | Leu | Asn | Ser | Leu | Thr | Tyr | Gln | Val | Leu | Asp | Val | Gln | |
| | | | 370 | | | | 375 | | | | | 380 | | | | |
| AGA | TAC | CCA | TTG | TAT | ACC | CAA | ATC | ACA | GTG | GAC | ATC | GGG | ACA | CCG | AGC | 1200 |
| Arg | Tyr | Pro | Leu | Tyr | Thr | Gln | Ile | Thr | Val | Asp | Ile | Gly | Thr | Pro | Ser | |
| | | 385 | | | | | 390 | | | | | 395 | | | | |

TAGGACTTTT GGTACAGGTA AAGACTGAAT TCATCGATAT CTAGATCTCG AGCTCGCGAA 1260

AGCTT 1265

(2) INFORMATION FOR SEQ ID NO: 2:

(i) SEQUENCE CHARACTERISTICS:
        (A) LENGTH: 398 amino acids
        (B) TYPE: amino acid
        (D) TOPOLOGY: linear (ii) MOLECULE TYPE: protein (xi) SEQUENCE DESCRIPTION: SEQ ID NO: 2:

| | | | | | | | | | | | | | | |
|---|---|---|---|---|---|---|---|---|---|---|---|---|---|---|
| Met | Arg | Leu | Arg | Glu | Pro | Leu | Leu | Ser | Gly | Ser | Ala | Ala | Met | Pro | Gly |
| 1 | | | | 5 | | | | | 10 | | | | | 15 | |
| Ala | Ser | Leu | Gln | Arg | Ala | Cys | Arg | Leu | Leu | Val | Ala | Val | Cys | Ala | Leu |
| | | | 20 | | | | | 25 | | | | | 30 | | |
| His | Leu | Gly | Val | Thr | Leu | Val | Tyr | Tyr | Leu | Ala | Gly | Arg | Asp | Leu | Ser |
| | | 35 | | | | | 40 | | | | | 45 | | | |
| Arg | Leu | Pro | Gln | Leu | Val | Gly | Val | Ser | Thr | Pro | Leu | Gln | Gly | Gly | Ser |
| | 50 | | | | | 55 | | | | | 60 | | | | |
| Asn | Ser | Ala | Ala | Ala | Ile | Gly | Gln | Ser | Ser | Gly | Glu | Leu | Arg | Thr | Gly |
| 65 | | | | | 70 | | | | | 75 | | | | | 80 |
| Gly | Ala | Arg | Pro | Pro | Pro | Leu | Gly | Ala | Ser | Ser | Gln | Pro | Arg | Pro |
| | | | | 85 | | | | | 90 | | | | | 95 |
| Gly | Gly | Asp | Ser | Ser | Pro | Val | Val | Asp | Ser | Gly | Pro | Gly | Pro | Ala | Ser |
| | | | 100 | | | | | 105 | | | | | 110 | | |
| Asn | Leu | Thr | Ser | Val | Pro | Val | Pro | His | Thr | Thr | Ala | Leu | Ser | Leu | Pro |
| | | 115 | | | | | 120 | | | | | 125 | | | |
| Ala | Cys | Pro | Glu | Glu | Ser | Pro | Leu | Leu | Val | Gly | Pro | Met | Leu | Ile | Glu |
| | 130 | | | | | 135 | | | | | 140 | | | | |
| Phe | Asn | Met | Pro | Val | Asp | Leu | Glu | Leu | Val | Ala | Lys | Gln | Asn | Pro | Asn |
| 145 | | | | | 150 | | | | | 155 | | | | | 160 |
| Val | Lys | Met | Gly | Gly | Arg | Tyr | Ala | Pro | Arg | Asp | Cys | Val | Ser | Pro | His |
| | | | | 165 | | | | | 170 | | | | | 175 | |
| Lys | Val | Ala | Ile | Ile | Ile | Pro | Phe | Arg | Asn | Arg | Gln | Glu | His | Leu | Lys |
| | | | 180 | | | | | 185 | | | | | 190 | | |
| Tyr | Trp | Leu | Tyr | Tyr | Leu | His | Pro | Val | Leu | Gln | Arg | Gln | Gln | Leu | Asp |
| | | 195 | | | | | 200 | | | | | 205 | | | |
| Tyr | Gly | Ile | Tyr | Val | Ile | Asn | Gln | Ala | Gly | Asp | Thr | Ile | Phe | Asn | Arg |
| | 210 | | | | | 215 | | | | | 220 | | | | |
| Ala | Lys | Leu | Leu | Asn | Val | Gly | Phe | Gln | Glu | Ala | Leu | Lys | Asp | Tyr | Asp |
| 225 | | | | | 230 | | | | | 235 | | | | | 240 |
| Tyr | Thr | Cys | Phe | Val | Phe | Ser | Asp | Val | Asp | Leu | Ile | Pro | Met | Asn | Asp |
| | | | | 245 | | | | | 250 | | | | | 255 | |

| | | | | | | | | | | | | | | | |
|---|---|---|---|---|---|---|---|---|---|---|---|---|---|---|---|
| His | Asn | Ala | Tyr 260 | Arg | Cys | Phe | Ser | Gln 265 | Pro | Arg | His | Ile | Ser 270 | Val | Ala |
| Met | Asp | Lys 275 | Phe | Gly | Phe | Ser | Leu | Pro 280 | Tyr | Val | Gln | Tyr | Phe 285 | Gly | Gly |
| Val | Ser 290 | Ala | Leu | Ser | Lys | Gln 295 | Gln | Phe | Leu | Thr | Ile 300 | Asn | Gly | Phe | Pro |
| Asn 305 | Asn | Tyr | Trp | Gly 310 | Trp | Gly | Glu | Asp | Asp 315 | Asp | Ile | Phe | Asn | Arg 320 | |
| Leu | Val | Phe | Arg | Gly 325 | Met | Ser | Ile | Ser | Arg 330 | Pro | Asn | Ala | Val | Val 335 | Gly |
| Arg | Cys | Arg | Met 340 | Ile | Arg | His | Ser | Arg 345 | Asp | Lys | Lys | Asn | Glu 350 | Pro | Asn |
| Pro | Gln | Arg 355 | Phe | Asp | Arg | Ile | Ala 360 | His | Thr | Lys | Glu | Thr 365 | Met | Leu | Ser |
| Asp | Gly 370 | Leu | Asn | Ser | Leu | Thr 375 | Tyr | Gln | Val | Leu | Asp 380 | Val | Gln | Arg | Tyr |
| Pro 385 | Leu | Tyr | Thr | Gln | Ile 390 | Thr | Val | Asp | Ile | Gly 395 | Thr | Pro | Ser | | |

(2) INFORMATION FOR SEQ ID NO: 3:

(i) SEQUENCE CHARACTERISTICS:
        (A) LENGTH: 1246 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (B) STRAIN: E. coli DH5alpha (vii) IMMEDIATE SOURCE:
        (B) CLONE: pSIA2

(ix) FEATURE:
        (A) NAME/KEY: CDS
        (B) LOCATION: 15..1232
        (D) OTHER INFORMATION: /product="full-length
        sialyltransferase (EC 2.4.99.1)"

(xi) SEQUENCE DESCRIPTION: SEQ ID NO: 3:

| | | | | | | | | | | | | | | |
|---|---|---|---|---|---|---|---|---|---|---|---|---|---|---|
| CTGCAGAATT | CAAA | ATG | ATT | CAC | ACC | AAC | CTG | AAG | AAA | AAG | TTC | AGC | TGC | 50 |
| | | Met 1 | Ile | His | Thr | Asn 5 | Leu | Lys | Lys | Lys | Phe | Ser 10 | Cys | |
| TGC | GTC | CTG | GTC | TTT | CTT | CTG | TTT | GCA | GTC | ATC | TGT | GTG | TGG | AAG | GAA | 98 |
| Cys | Val | Leu | Val 15 | Phe | Leu | Leu | Phe | Ala 20 | Val | Ile | Cys | Val | Trp 25 | Lys | Glu |
| AAG | AAG | AAA | GGG | AGT | TAC | TAT | GAT | TCC | TTT | AAA | TTG | CAA | ACC | AAG | GAA | 146 |
| Lys | Lys | Lys 30 | Gly | Ser | Tyr | Tyr | Asp 35 | Ser | Phe | Lys | Leu | Gln 40 | Thr | Lys | Glu |
| TTC | CAG | GTG | TTA | AAG | AGT | CTG | GGG | AAA | TTG | GCC | ATG | GGG | TCT | GAT | TCC | 194 |
| Phe 45 | Gln | Val | Leu | Lys | Ser 50 | Leu | Gly | Lys | Leu | Ala 55 | Met | Gly | Ser | Asp | Ser 60 |
| CAG | TCT | GTA | TCC | TCA | AGC | AGC | ACC | CAG | GAC | CCC | CAC | AGG | GGC | CGC | CAG | 242 |
| Gln | Ser | Val | Ser | Ser 65 | Ser | Ser | Thr | Gln | Asp 70 | Pro | His | Arg | Gly | Arg 75 | Gln |
| ACC | CTC | GGC | AGT | CTC | AGA | GGC | CTA | GCC | AAG | GCC | AAA | CCA | GAG | GCC | TCC | 290 |
| Thr | Leu | Gly | Ser 80 | Leu | Arg | Gly | Leu | Ala 85 | Lys | Ala | Lys | Pro | Glu 90 | Ala | Ser |
| TTC | CAG | GTG | TGG | AAC | AAG | GAC | AGC | TCT | TCC | AAA | AAC | CTT | ATC | CCT | AGG | 338 |
| Phe | Gln | Val 95 | Trp | Asn | Lys | Asp | Ser 100 | Ser | Ser | Lys | Asn | Leu 105 | Ile | Pro | Arg |

-continued

| | | | | | | | | | | | | | | | | |
|---|---|---|---|---|---|---|---|---|---|---|---|---|---|---|---|---|
| CTG | CAA | AAG | ATC | TGG | AAG | AAT | TAC | CTA | AGC | ATG | AAC | AAG | TAC | AAA | GTG | 386 |
| Leu | Gln | Lys | Ile | Trp | Lys | Asn | Tyr | Leu | Ser | Met | Asn | Lys | Tyr | Lys | Val | |
| | 110 | | | | 115 | | | | | 120 | | | | | | |
| TCC | TAC | AAG | GGG | CCA | GGA | CCA | GGC | ATC | AAG | TTC | AGT | GCA | GAG | GCC | CTG | 434 |
| Ser | Tyr | Lys | Gly | Pro | Gly | Pro | Gly | Ile | Lys | Phe | Ser | Ala | Glu | Ala | Leu | |
| 125 | | | | | 130 | | | | | 135 | | | | | 140 | |
| CGC | TGC | CAC | CTC | CGG | GAC | CAT | GTG | AAT | GTA | TCC | ATG | GTA | GAG | GTC | ACA | 482 |
| Arg | Cys | His | Leu | Arg | Asp | His | Val | Asn | Val | Ser | Met | Val | Glu | Val | Thr | |
| | | | | 145 | | | | | 150 | | | | | 155 | | |
| GAT | TTT | CCC | TTC | AAT | ACC | TCT | GAA | TGG | GAG | GGT | TAT | CTG | CCC | AAG | GAG | 530 |
| Asp | Phe | Pro | Phe | Asn | Thr | Ser | Glu | Trp | Glu | Gly | Tyr | Leu | Pro | Lys | Glu | |
| | | | | 160 | | | | | 165 | | | | | 170 | | |
| AGC | ATT | AGG | ACC | AAG | GCT | GGG | CCT | TGG | GGC | AGG | TGT | GCT | GTT | GTG | TCG | 578 |
| Ser | Ile | Arg | Thr | Lys | Ala | Gly | Pro | Trp | Gly | Arg | Cys | Ala | Val | Val | Ser | |
| | | 175 | | | | | 180 | | | | | 185 | | | | |
| TCA | GCG | GGA | TCT | CTG | AAG | TCC | TCC | CAA | CTA | GGC | AGA | GAA | ATC | GAT | GAT | 626 |
| Ser | Ala | Gly | Ser | Leu | Lys | Ser | Ser | Gln | Leu | Gly | Arg | Glu | Ile | Asp | Asp | |
| | 190 | | | | | 195 | | | | | 200 | | | | | |
| CAT | GAC | GCA | GTC | CTG | AGG | TTT | AAT | GGG | GCA | CCC | ACA | GCC | AAC | TTC | CAA | 674 |
| His | Asp | Ala | Val | Leu | Arg | Phe | Asn | Gly | Ala | Pro | Thr | Ala | Asn | Phe | Gln | |
| 205 | | | | | 210 | | | | | 215 | | | | | 220 | |
| CAA | GAT | GTG | GGC | ACA | AAA | ACT | ACC | ATT | CGC | CTG | ATG | AAC | TCT | CAG | TTG | 722 |
| Gln | Asp | Val | Gly | Thr | Lys | Thr | Thr | Ile | Arg | Leu | Met | Asn | Ser | Gln | Leu | |
| | | | | 225 | | | | | 230 | | | | | 235 | | |
| GTT | ACC | ACA | GAG | AAG | CGC | TTC | CTC | AAA | GAC | AGT | TTG | TAC | AAT | GAA | GGA | 770 |
| Val | Thr | Thr | Glu | Lys | Arg | Phe | Leu | Lys | Asp | Ser | Leu | Tyr | Asn | Glu | Gly | |
| | | | 240 | | | | | 245 | | | | | 250 | | | |
| ATC | CTA | ATT | GTA | TGG | GAC | CCA | TCT | GTA | TAC | CAC | TCA | GAT | ATC | CCA | AAG | 818 |
| Ile | Leu | Ile | Val | Trp | Asp | Pro | Ser | Val | Tyr | His | Ser | Asp | Ile | Pro | Lys | |
| | | 255 | | | | | 260 | | | | | 265 | | | | |
| TGG | TAC | CAG | AAT | CCG | GAT | TAT | AAT | TTC | TTT | AAC | AAC | TAC | AAG | ACT | TAT | 866 |
| Trp | Tyr | Gln | Asn | Pro | Asp | Tyr | Asn | Phe | Phe | Asn | Asn | Tyr | Lys | Thr | Tyr | |
| | 270 | | | | | 275 | | | | | 280 | | | | | |
| CGT | AAG | CTG | CAC | CCC | AAT | CAG | CCC | TTT | TAC | ATC | CTC | AAG | CCC | CAG | ATG | 914 |
| Arg | Lys | Leu | His | Pro | Asn | Gln | Pro | Phe | Tyr | Ile | Leu | Lys | Pro | Gln | Met | |
| 285 | | | | | 290 | | | | | 295 | | | | | 300 | |
| CCT | TGG | GAG | CTA | TGG | GAC | ATT | CTT | CAA | GAA | ATC | TCC | CCA | GAA | GAG | ATT | 962 |
| Pro | Trp | Glu | Leu | Trp | Asp | Ile | Leu | Gln | Glu | Ile | Ser | Pro | Glu | Glu | Ile | |
| | | | | 305 | | | | | 310 | | | | | 315 | | |
| CAG | CCA | AAC | CCC | CCA | TCC | TCT | GGG | ATG | CTT | GGT | ATC | ATC | ATC | ATG | ATG | 1010 |
| Gln | Pro | Asn | Pro | Pro | Ser | Ser | Gly | Met | Leu | Gly | Ile | Ile | Ile | Met | Met | |
| | | | 320 | | | | | 325 | | | | | 330 | | | |
| ACG | CTG | TGT | GAC | CAG | GTG | GAT | ATT | TAT | GAG | TTC | CTC | CCA | TCC | AAG | CGC | 1058 |
| Thr | Leu | Cys | Asp | Gln | Val | Asp | Ile | Tyr | Glu | Phe | Leu | Pro | Ser | Lys | Arg | |
| | | 335 | | | | | 340 | | | | | 345 | | | | |
| AAG | ACT | GAC | GTG | TGC | TAC | TAC | TAC | CAG | AAG | TTC | TTC | GAT | AGT | GCC | TGC | 1106 |
| Lys | Thr | Asp | Val | Cys | Tyr | Tyr | Tyr | Gln | Lys | Phe | Phe | Asp | Ser | Ala | Cys | |
| | 350 | | | | | 355 | | | | | 360 | | | | | |
| ACG | ATG | GGT | GCC | TAC | CAC | CCG | CTG | CTC | TAT | GAG | AAG | AAT | TTG | GTG | AAG | 1154 |
| Thr | Met | Gly | Ala | Tyr | His | Pro | Leu | Leu | Tyr | Glu | Lys | Asn | Leu | Val | Lys | |
| 365 | | | | | 370 | | | | | 375 | | | | | 380 | |
| CAT | CTC | AAC | CAG | GGC | ACA | GAT | GAG | GAC | ATC | TAC | CTG | CTT | GGA | AAA | GCC | 1202 |
| His | Leu | Asn | Gln | Gly | Thr | Asp | Glu | Asp | Ile | Tyr | Leu | Leu | Gly | Lys | Ala | |
| | | | | 385 | | | | | 390 | | | | | 395 | | |
| ACA | CTG | CCT | GGC | TTC | CGG | ACC | ATT | CAC | TGC | TAAGCACAGG ATCC | | | | | | 1246 |
| Thr | Leu | Pro | Gly | Phe | Arg | Thr | Ile | His | Cys | | | | | | | |
| | | | 400 | | | | | 405 | | | | | | | | |

( 2 ) INFORMATION FOR SEQ ID NO: 4:

(i) SEQUENCE CHARACTERISTICS:
 (A) LENGTH: 406 amino acids
 (B) TYPE: amino acid
 (D) TOPOLOGY: linear (ii) MOLECULE TYPE: protein (xi) SEQUENCE DESCRIPTION: SEQ ID NO: 4:

```
Met Ile His Thr Asn Leu Lys Lys Lys Phe Ser Cys Cys Val Leu Val
 1               5                  10                 15
Phe Leu Leu Phe Ala Val Ile Cys Val Trp Lys Glu Lys Lys Lys Gly
                20                  25                 30
Ser Tyr Tyr Asp Ser Phe Lys Leu Gln Thr Lys Glu Phe Gln Val Leu
            35                  40                 45
Lys Ser Leu Gly Lys Leu Ala Met Gly Ser Asp Ser Gln Ser Val Ser
        50                  55                 60
Ser Ser Ser Thr Gln Asp Pro His Arg Gly Arg Gln Thr Leu Gly Ser
65                  70                  75                 80
Leu Arg Gly Leu Ala Lys Ala Lys Pro Glu Ala Ser Phe Gln Val Trp
                85                  90                 95
Asn Lys Asp Ser Ser Ser Lys Asn Leu Ile Pro Arg Leu Gln Lys Ile
                100                 105                110
Trp Lys Asn Tyr Leu Ser Met Asn Lys Tyr Lys Val Ser Tyr Lys Gly
            115                 120                125
Pro Gly Pro Gly Ile Lys Phe Ser Ala Glu Ala Leu Arg Cys His Leu
        130                 135                140
Arg Asp His Val Asn Val Ser Met Val Glu Val Thr Asp Phe Pro Phe
145                 150                 155                160
Asn Thr Ser Glu Trp Glu Gly Tyr Leu Pro Lys Glu Ser Ile Arg Thr
                165                 170                175
Lys Ala Gly Pro Trp Gly Arg Cys Ala Val Val Ser Ser Ala Gly Ser
                180                 185                190
Leu Lys Ser Ser Gln Leu Gly Arg Glu Ile Asp Asp His Asp Ala Val
            195                 200                205
Leu Arg Phe Asn Gly Ala Pro Thr Ala Asn Phe Gln Gln Asp Val Gly
    210                 215                 220
Thr Lys Thr Thr Ile Arg Leu Met Asn Ser Gln Leu Val Thr Thr Glu
225                 230                 235                240
Lys Arg Phe Leu Lys Asp Ser Leu Tyr Asn Glu Gly Ile Leu Ile Val
                245                 250                255
Trp Asp Pro Ser Val Tyr His Ser Asp Ile Pro Lys Trp Tyr Gln Asn
            260                 265                270
Pro Asp Tyr Asn Phe Phe Asn Asn Tyr Lys Thr Tyr Arg Lys Leu His
        275                 280                285
Pro Asn Gln Pro Phe Tyr Ile Leu Lys Pro Gln Met Pro Trp Glu Leu
    290                 295                 300
Trp Asp Ile Leu Gln Glu Ile Ser Pro Glu Glu Ile Gln Pro Asn Pro
305                 310                 315                320
Pro Ser Ser Gly Met Leu Gly Ile Ile Ile Met Met Thr Leu Cys Asp
                325                 330                335
Gln Val Asp Ile Tyr Glu Phe Leu Pro Ser Lys Arg Lys Thr Asp Val
            340                 345                350
Cys Tyr Tyr Tyr Gln Lys Phe Phe Asp Ser Ala Cys Thr Met Gly Ala
        355                 360                365
Tyr His Pro Leu Leu Tyr Glu Lys Asn Leu Val Lys His Leu Asn Gln
    370                 375                 380
```

```
Gly  Thr  Asp  Glu  Asp  Ile  Tyr  Leu  Leu  Gly  Lys  Ala  Thr  Leu  Pro  Gly
385                      390                      395                      400

Phe  Arg  Thr  Ile  His  Cys
                    405
```

( 2 ) INFORMATION FOR SEQ ID NO: 5:

( i ) SEQUENCE CHARACTERISTICS:
        ( A ) LENGTH: 2304 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( B ) STRAIN: E. coli DH5alpha ( v i i ) IMMEDIATE SOURCE:
        ( B ) CLONE: YEPGSTa ( i x ) FEATURE:
        ( A ) NAME/KEY: CDS
        ( B ) LOCATION: 1..2301
        ( D ) OTHER INFORMATION: /product=
            " galactosyltransferase-sialyltransferase hybrid
            protein"

( x i ) SEQUENCE DESCRIPTION: SEQ ID NO: 5:

```
ATG  AGG  CTT  CGG  GAG  CCG  CTC  CTG  AGC  GGC  AGC  GCC  GCG  ATG  CCA  GGC    48
Met  Arg  Leu  Arg  Glu  Pro  Leu  Leu  Ser  Gly  Ser  Ala  Ala  Met  Pro  Gly
 1                  5                      10                      15

GCG  TCC  CTA  CAG  CGG  GCC  TGC  CGC  CTG  CTC  GTG  GCC  GTC  TGC  GCT  CTG    96
Ala  Ser  Leu  Gln  Arg  Ala  Cys  Arg  Leu  Leu  Val  Ala  Val  Cys  Ala  Leu
                20                      25                      30

CAC  CTT  GGC  GTC  ACC  CTC  GTT  TAC  TAC  CTG  GCT  GGC  CGC  GAC  CTG  AGC   144
His  Leu  Gly  Val  Thr  Leu  Val  Tyr  Tyr  Leu  Ala  Gly  Arg  Asp  Leu  Ser
           35                      40                      45

CGC  CTG  CCC  CAA  CTG  GTC  GGA  GTC  TCC  ACA  CCG  CTG  CAG  GGC  GGC  TCG   192
Arg  Leu  Pro  Gln  Leu  Val  Gly  Val  Ser  Thr  Pro  Leu  Gln  Gly  Gly  Ser
      50                      55                      60

AAC  AGT  GCC  GCC  GCC  ATC  GGG  CAG  TCC  TCC  GGG  GAG  CTC  CGG  ACC  GGA   240
Asn  Ser  Ala  Ala  Ala  Ile  Gly  Gln  Ser  Ser  Gly  Glu  Leu  Arg  Thr  Gly
 65                      70                      75                      80

GGG  GCC  CGG  CCG  CCG  CCT  CCT  CTA  GGC  GCC  TCC  TCC  CAG  CCG  CGC  CCG   288
Gly  Ala  Arg  Pro  Pro  Pro  Pro  Leu  Gly  Ala  Ser  Ser  Gln  Pro  Arg  Pro
                     85                      90                      95

GGT  GGC  GAC  TCC  AGC  CCA  GTC  GTG  GAT  TCT  GGC  CCT  GGC  CCC  GCT  AGC   336
Gly  Gly  Asp  Ser  Ser  Pro  Val  Val  Asp  Ser  Gly  Pro  Gly  Pro  Ala  Ser
                100                     105                     110

AAC  TTG  ACC  TCG  GTC  CCA  GTG  CCC  CAC  ACC  ACC  GCA  CTG  TCG  CTG  CCC   384
Asn  Leu  Thr  Ser  Val  Pro  Val  Pro  His  Thr  Thr  Ala  Leu  Ser  Leu  Pro
           115                     120                     125

GCC  TGC  CCT  GAG  GAG  TCC  CCG  CTG  CTT  GTG  GGC  CCC  ATG  CTG  ATT  GAG   432
Ala  Cys  Pro  Glu  Glu  Ser  Pro  Leu  Leu  Val  Gly  Pro  Met  Leu  Ile  Glu
      130                     135                     140

TTT  AAC  ATG  CCT  GTG  GAC  CTG  GAG  CTC  GTG  GCA  AAG  CAG  AAC  CCA  AAT   480
Phe  Asn  Met  Pro  Val  Asp  Leu  Glu  Leu  Val  Ala  Lys  Gln  Asn  Pro  Asn
145                     150                     155                     160

GTG  AAG  ATG  GGC  GGC  CGC  TAT  GCC  CCC  AGG  GAC  TGC  GTC  TCT  CCT  CAC   528
Val  Lys  Met  Gly  Gly  Arg  Tyr  Ala  Pro  Arg  Asp  Cys  Val  Ser  Pro  His
                     165                     170                     175

AAG  GTG  GCC  ATC  ATC  ATT  CCA  TTC  CGC  AAC  CGG  CAG  GAG  CAC  CTC  AAG   576
Lys  Val  Ala  Ile  Ile  Ile  Pro  Phe  Arg  Asn  Arg  Gln  Glu  His  Leu  Lys
                180                     185                     190
```

```
TAC TGG CTA TAT TAT TTG CAC CCA GTC CTG CAG CGC CAG CAG CTG GAC    624
Tyr Trp Leu Tyr Tyr Leu His Pro Val Leu Gln Arg Gln Gln Leu Asp
    195             200             205

TAT GGC ATC TAT GTT ATC AAC CAG GCG GGA GAC ACT ATA TTC AAT CGT    672
Tyr Gly Ile Tyr Val Ile Asn Gln Ala Gly Asp Thr Ile Phe Asn Arg
    210             215             220

GCT AAG CTC CTC AAT GTT GGC TTT CAA GAA GCC TTG AAG GAC TAT GAC    720
Ala Lys Leu Leu Asn Val Gly Phe Gln Glu Ala Leu Lys Asp Tyr Asp
225             230             235             240

TAC ACC TGC TTT GTG TTT AGT GAC GTG GAC CTC ATT CCA ATG AAT GAC    768
Tyr Thr Cys Phe Val Phe Ser Asp Val Asp Leu Ile Pro Met Asn Asp
                245             250             255

CAT AAT GCG TAC AGG TGT TTT TCA CAG CCA CGG CAC ATT TCC GTT GCA    816
His Asn Ala Tyr Arg Cys Phe Ser Gln Pro Arg His Ile Ser Val Ala
        260             265             270

ATG GAT AAG TTT GGA TTC AGC CTA CCT TAT GTT CAG TAT TTT GGA GGT    864
Met Asp Lys Phe Gly Phe Ser Leu Pro Tyr Val Gln Tyr Phe Gly Gly
        275             280             285

GTC TCT GCT CTA AGT AAA CAA CAG TTT CTA ACC ATC AAT GGA TTT CCT    912
Val Ser Ala Leu Ser Lys Gln Gln Phe Leu Thr Ile Asn Gly Phe Pro
    290             295             300

AAT AAT TAT TGG GGC TGG GGA GGA GAA GAT GAT GAC ATT TTT AAC AGA    960
Asn Asn Tyr Trp Gly Trp Gly Gly Glu Asp Asp Asp Ile Phe Asn Arg
305             310             315             320

TTA GTT TTT AGA GGC ATG TCT ATA TCT CGC CCA AAT GCT GTG GTC GGG   1008
Leu Val Phe Arg Gly Met Ser Ile Ser Arg Pro Asn Ala Val Val Gly
                325             330             335

AGG TGT CGC ATG ATC CGC CAC TCA AGA GAC AAG AAA AAT GAA CCC AAT   1056
Arg Cys Arg Met Ile Arg His Ser Arg Asp Lys Lys Asn Glu Pro Asn
        340             345             350

CCT CAG AGG TTT GAC CGA ATT GCA CAC ACA AAG GAG ACA ATG CTC TCT   1104
Pro Gln Arg Phe Asp Arg Ile Ala His Thr Lys Glu Thr Met Leu Ser
        355             360             365

GAT GGT TTG AAC TCA CTC ACC TAC CAG GTG CTG GAT GTA CAG AGA TAC   1152
Asp Gly Leu Asn Ser Leu Thr Tyr Gln Val Leu Asp Val Gln Arg Tyr
    370             375             380

CCA TTG TAT ACC CAA ATC ACA GTG GAC ATC GGG ACA CGA GCT GGG ATC   1200
Pro Leu Tyr Thr Gln Ile Thr Val Asp Ile Gly Thr Arg Ala Gly Ile
385             390             395             400

CGT CGA CCT GCA GAA TTC CAG GTG TTA AAG AGT CTG GGA AAA TTG GCC   1248
Arg Arg Pro Ala Glu Phe Gln Val Leu Lys Ser Leu Gly Lys Leu Ala
                405             410             415

ATG GGG TCT GAT TCC CAG TCT GTA TCC TCA AGC AGC ACC CAG GAC CCC   1296
Met Gly Ser Asp Ser Gln Ser Val Ser Ser Ser Ser Thr Gln Asp Pro
            420             425             430

CAC AGG GGC CGC CAG ACC CTC GGC AGT CTC AGA GGC CTA GCC AAG GCC   1344
His Arg Gly Arg Gln Thr Leu Gly Ser Leu Arg Gly Leu Ala Lys Ala
        435             440             445

AAA CCA GAG GCC TCC TTC CAG GTG TGG AAC AAG GAC AGC TCT TCC AAA   1392
Lys Pro Glu Ala Ser Phe Gln Val Trp Asn Lys Asp Ser Ser Ser Lys
450             455             460

AAC CTT ATC CCT AGG CTG CAA AAG ATC TGG AAG AAT TAC CTA AGC ATG   1440
Asn Leu Ile Pro Arg Leu Gln Lys Ile Trp Lys Asn Tyr Leu Ser Met
465             470             475             480

AAC AAG TAC AAA GTG TCC TAC AAG GGG CCA GGA CCA GGC ATC AAG TTC   1488
Asn Lys Tyr Lys Val Ser Tyr Lys Gly Pro Gly Pro Gly Ile Lys Phe
                485             490             495

AGT GCA GAG GCC CTG CGC TGC CAC CTC CGG GAC CAT GTG AAT GTA TCC   1536
Ser Ala Glu Ala Leu Arg Cys His Leu Arg Asp His Val Asn Val Ser
            500             505             510
```

| | | | | | | | | | | | | | | | | |
|---|---|---|---|---|---|---|---|---|---|---|---|---|---|---|---|---|
|ATG|GTA|GAG|GTC|ACA|GAT|TTT|CCC|TTC|AAT|ACC|TCT|GAA|TGG|GAG|GGT|1584|
|Met|Val|Glu|Val|Thr|Asp|Phe|Pro|Phe|Asn|Thr|Ser|Glu|Trp|Glu|Gly| |
| | |515| | | |520| | | |525| | | | | | |
|TAT|CTG|CCC|AAG|GAG|AGC|ATT|AGG|ACC|AAG|GCT|GGG|CCT|TGG|GGC|AGG|1632|
|Tyr|Leu|Pro|Lys|Glu|Ser|Ile|Arg|Thr|Lys|Ala|Gly|Pro|Trp|Gly|Arg| |
| |530| | | | |535| | | | |540| | | | | |
|TGT|GCT|GTT|GTG|TCG|TCA|GCG|GGA|TCT|CTG|AAG|TCC|TCC|CAA|CTA|GGC|1680|
|Cys|Ala|Val|Val|Ser|Ser|Ala|Gly|Ser|Leu|Lys|Ser|Ser|Gln|Leu|Gly| |
|545| | | | |550| | | | |555| | | | |560| |
|AGA|GAA|ATC|GAT|GAT|CAT|GAC|GCA|GTC|CTG|AGG|TTT|AAT|GGG|GCA|CCC|1728|
|Arg|Glu|Ile|Asp|Asp|His|Asp|Ala|Val|Leu|Arg|Phe|Asn|Gly|Ala|Pro| |
| | | | |565| | | | |570| | | | |575| | |
|ACA|GCC|AAC|TTC|CAA|CAA|GAT|GTG|GGC|ACA|AAA|ACT|ACC|ATT|CGC|CTG|1776|
|Thr|Ala|Asn|Phe|Gln|Gln|Asp|Val|Gly|Thr|Lys|Thr|Thr|Ile|Arg|Leu| |
| | | |580| | | | |585| | | | |590| | | |
|ATG|AAC|TCT|CAG|TTG|GTT|ACC|ACA|GAG|AAG|CGC|TTC|CTC|AAA|GAC|AGT|1824|
|Met|Asn|Ser|Gln|Leu|Val|Thr|Thr|Glu|Lys|Arg|Phe|Leu|Lys|Asp|Ser| |
| | |595| | | | |600| | | | |605| | | | |
|TTG|TAC|AAT|GAA|GGA|ATC|CTA|ATT|GTA|TGG|GAC|CCA|TCT|GTA|TAC|CAC|1872|
|Leu|Tyr|Asn|Glu|Gly|Ile|Leu|Ile|Val|Trp|Asp|Pro|Ser|Val|Tyr|His| |
| |610| | | | |615| | | | |620| | | | | |
|TCA|GAT|ATC|CCA|AAG|TGG|TAC|CAG|AAT|CCG|GAT|TAT|AAT|TTC|TTT|AAC|1920|
|Ser|Asp|Ile|Pro|Lys|Trp|Tyr|Gln|Asn|Pro|Asp|Tyr|Asn|Phe|Phe|Asn| |
|625| | | | |630| | | | |635| | | | |640| |
|AAC|TAC|AAG|ACT|TAT|CGT|AAG|CTG|CAC|CCC|AAT|CAG|CCC|TTT|TAC|ATC|1968|
|Asn|Tyr|Lys|Thr|Tyr|Arg|Lys|Leu|His|Pro|Asn|Gln|Pro|Phe|Tyr|Ile| |
| | | | |645| | | | |650| | | | |655| | |
|CTC|AAG|CCC|CAG|ATG|CCT|TGG|GAG|CTA|TGG|GAC|ATT|CTT|CAA|GAA|ATC|2016|
|Leu|Lys|Pro|Gln|Met|Pro|Trp|Glu|Leu|Trp|Asp|Ile|Leu|Gln|Glu|Ile| |
| | | |660| | | | |665| | | | |670| | | |
|TCC|CCA|GAA|GAG|ATT|CAG|CCA|AAC|CCC|CCA|TCC|TCT|GGG|ATG|CTT|GGT|2064|
|Ser|Pro|Glu|Glu|Ile|Gln|Pro|Asn|Pro|Pro|Ser|Ser|Gly|Met|Leu|Gly| |
| | |675| | | | |680| | | | |685| | | | |
|ATC|ATC|ATC|ATG|ATG|ACG|CTG|TGT|GAC|CAG|GTG|GAT|ATT|TAT|GAG|TTC|2112|
|Ile|Ile|Ile|Met|Met|Thr|Leu|Cys|Asp|Gln|Val|Asp|Ile|Tyr|Glu|Phe| |
| |690| | | | |695| | | | |700| | | | | |
|CTC|CCA|TCC|AAG|CGC|AAG|ACT|GAC|GTG|TGC|TAC|TAC|TAC|CAG|AAG|TTC|2160|
|Leu|Pro|Ser|Lys|Arg|Lys|Thr|Asp|Val|Cys|Tyr|Tyr|Tyr|Gln|Lys|Phe| |
|705| | | | |710| | | | |715| | | | |720| |
|TTC|GAT|AGT|GCC|TGC|ACG|ATG|GGT|GCC|TAC|CAC|CCG|CTG|CTC|TAT|GAG|2208|
|Phe|Asp|Ser|Ala|Cys|Thr|Met|Gly|Ala|Tyr|His|Pro|Leu|Leu|Tyr|Glu| |
| | | | |725| | | | |730| | | | |735| | |
|AAG|AAT|TTG|GTG|AAG|CAT|CTC|AAC|CAG|GGC|ACA|GAT|GAG|GAC|ATC|TAC|2256|
|Lys|Asn|Leu|Val|Lys|His|Leu|Asn|Gln|Gly|Thr|Asp|Glu|Asp|Ile|Tyr| |
| | | |740| | | | |745| | | | |750| | | |
|CTG|CTT|GGA|AAA|GCC|ACA|CTG|CCT|GGC|TTC|CGG|ACC|ATT|CAC|TGC| |2301|
|Leu|Leu|Gly|Lys|Ala|Thr|Leu|Pro|Gly|Phe|Arg|Thr|Ile|His|Cys| | |
| | |755| | | | |760| | | | |765| | | | |
|TAA| | | | | | | | | | | | | | | |2304|

( 2 ) INFORMATION FOR SEQ ID NO: 6:

( i ) SEQUENCE CHARACTERISTICS:
        ( A ) LENGTH: 767 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 6:

Met  Arg  Leu  Arg  Glu  Pro  Leu  Leu  Ser  Gly  Ser  Ala  Ala  Met  Pro  Gly

|     | 1     |     |     |     | 5   |     |     |     |     | 10  |     |     |     |     | 15  |     |
| --- | ----- | --- | --- | --- | --- | --- | --- | --- | --- | --- | --- | --- | --- | --- | --- | --- |
| Ala | Ser   | Leu | Gln | Arg | Ala | Cys | Arg | Leu | Leu | Val | Ala | Val | Cys | Ala | Leu |     |
|     |       |     |     | 20  |     |     |     | 25  |     |     |     | 30  |     |     |     |     |
| His | Leu   | Gly | Val | Thr | Leu | Val | Tyr | Tyr | Leu | Ala | Gly | Arg | Asp | Leu | Ser |     |
|     |       | 35  |     |     |     | 40  |     |     |     | 45  |     |     |     |     |     |     |
| Arg | Leu   | Pro | Gln | Leu | Val | Gly | Val | Ser | Thr | Pro | Leu | Gln | Gly | Gly | Ser |     |
|     | 50    |     |     |     | 55  |     |     |     |     | 60  |     |     |     |     |     |     |
| Asn | Ser   | Ala | Ala | Ala | Ile | Gly | Gln | Ser | Ser | Gly | Glu | Leu | Arg | Thr | Gly |     |
| 65  |       |     |     |     | 70  |     |     |     |     | 75  |     |     |     |     | 80  |     |
| Gly | Ala   | Arg | Pro | Pro | Pro | Pro | Leu | Gly | Ala | Ser | Ser | Gln | Pro | Arg | Pro |     |
|     |       |     |     | 85  |     |     |     | 90  |     |     |     | 95  |     |     |     |     |
| Gly | Gly   | Asp | Ser | Ser | Pro | Val | Val | Asp | Ser | Gly | Pro | Gly | Pro | Ala | Ser |     |
|     |       |     | 100 |     |     |     | 105 |     |     |     | 110 |     |     |     |     |     |
| Asn | Leu   | Thr | Ser | Val | Pro | Val | Pro | His | Thr | Thr | Ala | Leu | Ser | Leu | Pro |     |
|     |       | 115 |     |     |     | 120 |     |     |     | 125 |     |     |     |     |     |     |
| Ala | Cys   | Pro | Glu | Glu | Ser | Pro | Leu | Leu | Val | Gly | Pro | Met | Leu | Ile | Glu |     |
|     | 130   |     |     |     | 135 |     |     |     |     | 140 |     |     |     |     |     |     |
| Phe | Asn   | Met | Pro | Val | Asp | Leu | Glu | Leu | Val | Ala | Lys | Gln | Asn | Pro | Asn |     |
| 145 |       |     |     | 150 |     |     |     | 155 |     |     |     | 160 |     |     |     |     |
| Val | Lys   | Met | Gly | Gly | Arg | Tyr | Ala | Pro | Arg | Asp | Cys | Val | Ser | Pro | His |     |
|     |       |     | 165 |     |     |     | 170 |     |     |     | 175 |     |     |     |     |     |
| Lys | Val   | Ala | Ile | Ile | Ile | Pro | Phe | Arg | Asn | Arg | Gln | Glu | His | Leu | Lys |     |
|     |       |     | 180 |     |     |     | 185 |     |     |     | 190 |     |     |     |     |     |
| Tyr | Trp   | Leu | Tyr | Tyr | Leu | His | Pro | Val | Leu | Gln | Arg | Gln | Gln | Leu | Asp |     |
|     |       | 195 |     |     |     | 200 |     |     |     | 205 |     |     |     |     |     |     |
| Tyr | Gly   | Ile | Tyr | Val | Ile | Asn | Gln | Ala | Gly | Asp | Thr | Ile | Phe | Asn | Arg |     |
|     | 210   |     |     |     | 215 |     |     |     |     | 220 |     |     |     |     |     |     |
| Ala | Lys   | Leu | Leu | Asn | Val | Gly | Phe | Gln | Glu | Ala | Leu | Lys | Asp | Tyr | Asp |     |
| 225 |       |     |     | 230 |     |     |     | 235 |     |     |     | 240 |     |     |     |     |
| Tyr | Thr   | Cys | Phe | Val | Phe | Ser | Asp | Val | Asp | Leu | Ile | Pro | Met | Asn | Asp |     |
|     |       |     | 245 |     |     |     | 250 |     |     |     | 255 |     |     |     |     |     |
| His | Asn   | Ala | Tyr | Arg | Cys | Phe | Ser | Gln | Pro | Arg | His | Ile | Ser | Val | Ala |     |
|     |       |     | 260 |     |     |     | 265 |     |     |     | 270 |     |     |     |     |     |
| Met | Asp   | Lys | Phe | Gly | Phe | Ser | Leu | Pro | Tyr | Val | Gln | Tyr | Phe | Gly | Gly |     |
|     |       | 275 |     |     |     | 280 |     |     |     | 285 |     |     |     |     |     |     |
| Val | Ser   | Ala | Leu | Ser | Lys | Gln | Gln | Phe | Leu | Thr | Ile | Asn | Gly | Phe | Pro |     |
|     | 290   |     |     |     | 295 |     |     |     |     | 300 |     |     |     |     |     |     |
| Asn | Asn   | Tyr | Trp | Gly | Trp | Gly | Gly | Glu | Asp | Asp | Ile | Phe | Asn | Arg |     |     |
| 305 |       |     |     |     | 310 |     |     |     | 315 |     |     |     |     | 320 |     |     |
| Leu | Val   | Phe | Arg | Gly | Met | Ser | Ile | Ser | Arg | Pro | Asn | Ala | Val | Val | Gly |     |
|     |       |     |     | 325 |     |     |     | 330 |     |     |     | 335 |     |     |     |     |
| Arg | Cys   | Arg | Met | Ile | Arg | His | Ser | Arg | Asp | Lys | Lys | Asn | Glu | Pro | Asn |     |
|     |       |     | 340 |     |     |     | 345 |     |     |     | 350 |     |     |     |     |     |
| Pro | Gln   | Arg | Phe | Asp | Arg | Ile | Ala | His | Thr | Lys | Glu | Thr | Met | Leu | Ser |     |
|     |       | 355 |     |     |     | 360 |     |     |     | 365 |     |     |     |     |     |     |
| Asp | Gly   | Leu | Asn | Ser | Leu | Thr | Tyr | Gln | Val | Leu | Asp | Val | Gln | Arg | Tyr |     |
|     | 370   |     |     |     | 375 |     |     |     |     | 380 |     |     |     |     |     |     |
| Pro | Leu   | Tyr | Thr | Gln | Ile | Thr | Val | Asp | Ile | Gly | Thr | Arg | Ala | Gly | Ile |     |
| 385 |       |     |     | 390 |     |     |     | 395 |     |     |     |     |     |     | 400 |     |
| Arg | Arg   | Pro | Ala | Glu | Phe | Gln | Val | Leu | Lys | Ser | Leu | Gly | Lys | Leu | Ala |     |
|     |       |     |     | 405 |     |     |     | 410 |     |     |     | 415 |     |     |     |     |
| Met | Gly   | Ser | Asp | Ser | Gln | Ser | Val | Ser | Ser | Ser | Thr | Gln | Asp | Pro |     |     |
|     |       |     | 420 |     |     |     | 425 |     |     |     | 430 |     |     |     |     |     |

| His | Arg | Gly     | Arg | Gln | Thr | Leu | Gly     | Ser | Leu | Arg | Gly | Leu     | Ala | Lys | Ala |
|     |     | 435     |     |     |     |     | 440     |     |     |     |     | 445     |     |     |     |
| Lys | Pro | Glu     | Ala | Ser | Phe | Gln | Val     | Trp | Asn | Lys | Asp | Ser     | Ser | Ser | Lys |
|     |     | 450     |     |     |     |     | 455     |     |     |     |     | 460     |     |     |     |
| Asn | Leu | Ile     | Pro | Arg | Leu | Gln | Lys     | Ile | Trp | Lys | Asn | Tyr     | Leu | Ser | Met |
| 465 |     |         |     |     | 470 |     |         |     |     | 475 |     |         |     |     | 480 |
| Asn | Lys | Tyr     | Lys | Val | Ser | Tyr | Lys     | Gly | Pro | Gly | Pro | Gly     | Ile | Lys | Phe |
|     |     |         |     | 485 |     |     |         |     | 490 |     |     |         |     | 495 |     |
| Ser | Ala | Glu     | Ala | Leu | Arg | Cys | His     | Leu | Arg | Asp | His | Val     | Asn | Val | Ser |
|     |     |         | 500 |     |     |     |         | 505 |     |     |     |         | 510 |     |     |
| Met | Val | Glu     | Val | Thr | Asp | Phe | Pro     | Phe | Asn | Thr | Ser | Glu     | Trp | Glu | Gly |
|     |     | 515     |     |     |     |     | 520     |     |     |     |     | 525     |     |     |     |
| Tyr | Leu | Pro     | Lys | Glu | Ser | Ile | Arg     | Thr | Lys | Ala | Gly | Pro     | Trp | Gly | Arg |
|     |     | 530     |     |     |     |     | 535     |     |     |     |     | 540     |     |     |     |
| Cys | Ala | Val     | Val | Ser | Ser | Ala | Gly     | Ser | Leu | Lys | Ser | Ser     | Gln | Leu | Gly |
| 545 |     |         |     |     | 550 |     |         |     |     | 555 |     |         |     |     | 560 |
| Arg | Glu | Ile     | Asp | Asp | His | Asp | Ala     | Val | Leu | Arg | Phe | Asn     | Gly | Ala | Pro |
|     |     |         |     | 565 |     |     |         |     | 570 |     |     |         |     | 575 |     |
| Thr | Ala | Asn     | Phe | Gln | Gln | Asp | Val     | Gly | Thr | Lys | Thr | Thr     | Ile | Arg | Leu |
|     |     |         | 580 |     |     |     |         | 585 |     |     |     |         | 590 |     |     |
| Met | Asn | Ser     | Gln | Leu | Val | Thr | Thr     | Glu | Lys | Arg | Phe | Leu     | Lys | Asp | Ser |
|     |     | 595     |     |     |     |     | 600     |     |     |     |     | 605     |     |     |     |
| Leu | Tyr | Asn     | Glu | Gly | Ile | Leu | Ile     | Val | Trp | Asp | Pro | Ser     | Val | Tyr | His |
|     |     | 610     |     |     |     |     | 615     |     |     |     |     | 620     |     |     |     |
| Ser | Asp | Ile     | Pro | Lys | Trp | Tyr | Gln     | Asn | Pro | Asp | Tyr | Asn     | Phe | Phe | Asn |
| 625 |     |         |     |     | 630 |     |         |     |     | 635 |     |         |     |     | 640 |
| Asn | Tyr | Lys     | Thr | Tyr | Arg | Lys | Leu     | His | Pro | Asn | Gln | Pro     | Phe | Tyr | Ile |
|     |     |         |     | 645 |     |     |         |     | 650 |     |     |         |     | 655 |     |
| Leu | Lys | Pro     | Gln | Met | Pro | Trp | Glu     | Leu | Trp | Asp | Ile | Leu     | Gln | Glu | Ile |
|     |     |         | 660 |     |     |     |         | 665 |     |     |     |         | 670 |     |     |
| Ser | Pro | Glu     | Glu | Ile | Gln | Pro | Asn     | Pro | Pro | Ser | Ser | Gly     | Met | Leu | Gly |
|     |     | 675     |     |     |     |     | 680     |     |     |     |     | 685     |     |     |     |
| Ile | Ile | Ile     | Met | Met | Thr | Leu | Cys     | Asp | Gln | Val | Asp | Ile     | Tyr | Glu | Phe |
|     |     | 690     |     |     |     |     | 695     |     |     |     |     | 700     |     |     |     |
| Leu | Pro | Ser     | Lys | Arg | Lys | Thr | Asp     | Val | Cys | Tyr | Tyr | Tyr     | Gln | Lys | Phe |
| 705 |     |         |     |     | 710 |     |         |     |     | 715 |     |         |     |     | 720 |
| Phe | Asp | Ser     | Ala | Cys | Thr | Met | Gly     | Ala | Tyr | His | Pro | Leu     | Leu | Tyr | Glu |
|     |     |         |     | 725 |     |     |         |     | 730 |     |     |         |     | 735 |     |
| Lys | Asn | Leu     | Val | Lys | His | Leu | Asn     | Gln | Gly | Thr | Asp | Glu     | Asp | Ile | Tyr |
|     |     |         | 740 |     |     |     |         | 745 |     |     |     |         | 750 |     |     |
| Leu | Leu | Gly     | Lys | Ala | Thr | Leu | Pro     | Gly | Phe | Arg | Thr | Ile     | His | Cys |     |
|     |     | 755     |     |     |     |     | 760     |     |     |     |     | 765     |     |     |     |

( 2 ) INFORMATION FOR SEQ ID NO: 7:

( i ) SEQUENCE CHARACTERISTICS:
        ( A ) LENGTH: 2304 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( B ) STRAIN: E. coli DH5alpha ( v i i ) IMMEDIATE SOURCE:
        ( B ) CLONE: YEPGSTb ( i x ) FEATURE:
    ( A ) NAME/KEY: CDS
    ( B ) LOCATION: 1..2301
    ( D ) OTHER INFORMATION: /product=
        "galactosyltransferase-sialyltransferase hybrid
        protein"

( x i ) SEQUENCE DESCRIPTION: SEQ ID NO: 7:

```
ATG AGG CTT CGG GAG CCG CTC CTG AGC GGC AGC GCC GCG ATG CCA GGC      48
Met Arg Leu Arg Glu Pro Leu Leu Ser Gly Ser Ala Ala Met Pro Gly
 1           5                  10                  15

GCG TCC CTA CAG CGG GCC TGC CGC CTG CTC GTG GCC GTC TGC GCT CTG      96
Ala Ser Leu Gln Arg Ala Cys Arg Leu Leu Val Ala Val Cys Ala Leu
             20                  25                  30

CAC CTT GGC GTC ACC CTC GTT TAC TAC CTG GCT GGC CGC GAC CTG AGC     144
His Leu Gly Val Thr Leu Val Tyr Tyr Leu Ala Gly Arg Asp Leu Ser
             35                  40                  45

CGC CTG CCC CAA CTG GTC GGA GTC TCC ACA CCG CTG CAG GGC GGC TCG     192
Arg Leu Pro Gln Leu Val Gly Val Ser Thr Pro Leu Gln Gly Gly Ser
 50                  55                  60

AAC AGT GCC GCC GCC ATC GGG CAG TCC TCC GGG GAG CTC CGG ACC GGA     240
Asn Ser Ala Ala Ala Ile Gly Gln Ser Ser Gly Glu Leu Arg Thr Gly
 65                  70                  75                  80

GGG GCC CGG CCG CCG CCT CCT CTA GGC GCC TCC TCC CAG CCG CGC CCG     288
Gly Ala Arg Pro Pro Pro Pro Leu Gly Ala Ser Ser Gln Pro Arg Pro
                 85                  90                  95

GGT GGC GAC TCC AGC CCA GTC GTG GAT TCT GGC CCT GGC CCC GCT AGC     336
Gly Gly Asp Ser Ser Pro Val Val Asp Ser Gly Pro Gly Pro Ala Ser
            100                 105                 110

AAC TTG ACC TCG GTC CCA GTG CCC CAC ACC ACC GCA CTG TCG CTG CCC     384
Asn Leu Thr Ser Val Pro Val Pro His Thr Thr Ala Leu Ser Leu Pro
            115                 120                 125

GCC TGC CCT GAG GAG TCC CCG CTG CTT GTG GGC CCC ATG CTG ATT GAG     432
Ala Cys Pro Glu Glu Ser Pro Leu Leu Val Gly Pro Met Leu Ile Glu
        130                 135                 140

TTT AAC ATG CCT GTG GAC CTG GAG CTC GTG GCA AAG CAG AAC CCA AAT     480
Phe Asn Met Pro Val Asp Leu Glu Leu Val Ala Lys Gln Asn Pro Asn
145                 150                 155                 160

GTG AAG ATG GGC GGC CGC TAT GCC CCC AGG GAC TGC GTC TCT CCT CAC     528
Val Lys Met Gly Gly Arg Tyr Ala Pro Arg Asp Cys Val Ser Pro His
                165                 170                 175

AAG GTG GCC ATC ATC ATT CCA TTC CGC AAC CGG CAG GAG CAC CTC AAG     576
Lys Val Ala Ile Ile Ile Pro Phe Arg Asn Arg Gln Glu His Leu Lys
            180                 185                 190

TAC TGG CTA TAT TAT TTG CAC CCA GTC CTG CAG CGC CAG CAG CTG GAC     624
Tyr Trp Leu Tyr Tyr Leu His Pro Val Leu Gln Arg Gln Gln Leu Asp
            195                 200                 205

TAT GGC ATC TAT GTT ATC AAC CAG GCG GGA GAC ACT ATA TTC AAT CGT     672
Tyr Gly Ile Tyr Val Ile Asn Gln Ala Gly Asp Thr Ile Phe Asn Arg
        210                 215                 220

GCT AAG CTC CTC AAT GTT GGC TTT CAA GAA GCC TTG AAG GAC TAT GAC     720
Ala Lys Leu Leu Asn Val Gly Phe Gln Glu Ala Leu Lys Asp Tyr Asp
225                 230                 235                 240

TAC ACC TGC TTT GTG TTT AGT GAC GTG GAC CTC ATT CCA ATG AAT GAC     768
Tyr Thr Cys Phe Val Phe Ser Asp Val Asp Leu Ile Pro Met Asn Asp
                245                 250                 255

CAT AAT GCG TAC AGG TGT TTT TCA CAG CCA CGG CAC ATT TCC GTT GCA     816
His Asn Ala Tyr Arg Cys Phe Ser Gln Pro Arg His Ile Ser Val Ala
            260                 265                 270

ATG GAT AAG TTT GGA TTC AGC CTA CCT TAT GTT CAG TAT TTT GGA GGT     864
Met Asp Lys Phe Gly Phe Ser Leu Pro Tyr Val Gln Tyr Phe Gly Gly
            275                 280                 285
```

```
GTC TCT GCT CTA AGT AAA CAA CAG TTT CTA ACC ATC AAT GGA TTT CCT    912
Val Ser Ala Leu Ser Lys Gln Gln Phe Leu Thr Ile Asn Gly Phe Pro
    290             295                 300

AAT AAT TAT TGG GGC TGG GGA GGA GAA GAT GAT GAC ATT TTT AAC AGA    960
Asn Asn Tyr Trp Gly Trp Gly Gly Glu Asp Asp Asp Ile Phe Asn Arg
305             310                 315                     320

TTA GTT TTT AGA GGC ATG TCT ATA TCT CGC CCA AAT GCT GTG GTC GGG   1008
Leu Val Phe Arg Gly Met Ser Ile Ser Arg Pro Asn Ala Val Val Gly
                325                 330                 335

AGG TGT CGC ATG ATC CGC CAC TCA AGA GAC AAG AAA AAT GAA CCC AAT   1056
Arg Cys Arg Met Ile Arg His Ser Arg Asp Lys Lys Asn Glu Pro Asn
                340             345                 350

CCT CAG AGG TTT GAC CGA ATT GCA CAC ACA AAG GAG ACA ATG CTC TCT   1104
Pro Gln Arg Phe Asp Arg Ile Ala His Thr Lys Glu Thr Met Leu Ser
        355                 360                 365

GAT GGT TTG AAC TCA CTC ACC TAC CAG GTG CTG GAT GTA CAG AGA TAC   1152
Asp Gly Leu Asn Ser Leu Thr Tyr Gln Val Leu Asp Val Gln Arg Tyr
    370                 375                 380

CCA TTG TAT ACC CAA ATC ACA GTG GAC ATC GGG ACA CGA GCT AGG ATC   1200
Pro Leu Tyr Thr Gln Ile Thr Val Asp Ile Gly Thr Arg Ala Arg Ile
385             390                 395                     400

CGT CGA CCT GCA GAA TTC CAG GTG TTA AAG AGT CTG GGG AAA TTG GCC   1248
Arg Arg Pro Ala Glu Phe Gln Val Leu Lys Ser Leu Gly Lys Leu Ala
                405                 410                 415

ATG GGG TCT GAT TCC CAG TCT GTA TCC TCA AGC AGC ACC CAG GAC CCC   1296
Met Gly Ser Asp Ser Gln Ser Val Ser Ser Ser Ser Thr Gln Asp Pro
                420                 425                 430

CAC AGG GGC CGC CAG ACC CTC GGC AGT CTC AGA GGC CTA GCC AAG GCC   1344
His Arg Gly Arg Gln Thr Leu Gly Ser Leu Arg Gly Leu Ala Lys Ala
        435                 440                 445

AAA CCA GAG GCC TCC TTC CAG GTG TGG AAC AAG GAC AGC TCT TCC AAA   1392
Lys Pro Glu Ala Ser Phe Gln Val Trp Asn Lys Asp Ser Ser Ser Lys
    450                 455                 460

AAC CTT ATC CCT AGG CTG CAA AAG ATC TGG AAG AAT TAC CTA AGC ATG   1440
Asn Leu Ile Pro Arg Leu Gln Lys Ile Trp Lys Asn Tyr Leu Ser Met
465             470                 475                     480

AAC AAG TAC AAA GTG TCC TAC AAG GGG CCA GGA CCA GGC ATC AAG TTC   1488
Asn Lys Tyr Lys Val Ser Tyr Lys Gly Pro Gly Pro Gly Ile Lys Phe
                485                 490                 495

AGT GCA GAG GCC CTG CGC TGC CAC CTC CGG GAC CAT GTG AAT GTA TCC   1536
Ser Ala Glu Ala Leu Arg Cys His Leu Arg Asp His Val Asn Val Ser
                500                 505                 510

ATG GTA GAG GTC ACA GAT TTT CCC TTC AAT ACC TCT GAA TGG GAG GGT   1584
Met Val Glu Val Thr Asp Phe Pro Phe Asn Thr Ser Glu Trp Glu Gly
        515                 520                 525

TAT CTG CCC AAG GAG AGC ATT AGG ACC AAG GCT GGG CCT TGG GGC AGG   1632
Tyr Leu Pro Lys Glu Ser Ile Arg Thr Lys Ala Gly Pro Trp Gly Arg
    530                 535                 540

TGT GCT GTT GTG TCG TCA GCG GGA TCT CTG AAG TCC TCC CAA CTA GGC   1680
Cys Ala Val Val Ser Ser Ala Gly Ser Leu Lys Ser Ser Gln Leu Gly
545             550                 555                     560

AGA GAA ATC GAT GAT CAT GAC GCA GTC CTG AGG TTT AAT GGG GCA CCC   1728
Arg Glu Ile Asp Asp His Asp Ala Val Leu Arg Phe Asn Gly Ala Pro
                565                 570                 575

ACA GCC AAC TTC CAA CAA GAT GTG GGC ACA AAA ACT ACC ATT CGC CTG   1776
Thr Ala Asn Phe Gln Gln Asp Val Gly Thr Lys Thr Thr Ile Arg Leu
                580                 585                 590

ATG AAC TCT CAG TTG GTT ACC ACA GAG AAG CGC TTC CTC AAA GAC AGT   1824
Met Asn Ser Gln Leu Val Thr Thr Glu Lys Arg Phe Leu Lys Asp Ser
        595                 600                 605
```

-continued

```
TTG TAC AAT GAA GGA ATC CTA ATT GTA TGG GAC CCA TCT GTA TAC CAC      1872
Leu Tyr Asn Glu Gly Ile Leu Ile Val Trp Asp Pro Ser Val Tyr His
    610                 615                 620

TCA GAT ATC CCA AAG TGG TAC CAG AAT CCG GAT TAT AAT TTC TTT AAC      1920
Ser Asp Ile Pro Lys Trp Tyr Gln Asn Pro Asp Tyr Asn Phe Phe Asn
625                 630                 635                 640

AAC TAC AAG ACT TAT CGT AAG CTG CAC CCC AAT CAG CCC TTT TAC ATC      1968
Asn Tyr Lys Thr Tyr Arg Lys Leu His Pro Asn Gln Pro Phe Tyr Ile
                645                 650                 655

CTC AAG CCC CAG ATG CCT TGG GAG CTA TGG GAC ATT CTT CAA GAA ATC      2016
Leu Lys Pro Gln Met Pro Trp Glu Leu Trp Asp Ile Leu Gln Glu Ile
            660                 665                 670

TCC CCA GAA GAG ATT CAG CCA AAC CCC CCA TCC TCT GGG ATG CTT GGT      2064
Ser Pro Glu Glu Ile Gln Pro Asn Pro Pro Ser Ser Gly Met Leu Gly
        675                 680                 685

ATC ATC ATC ATG ATG ACG CTG TGT GAC CAG GTG GAT ATT TAT GAG TTC      2112
Ile Ile Ile Met Met Thr Leu Cys Asp Gln Val Asp Ile Tyr Glu Phe
    690                 695                 700

CTC CCA TCC AAG CGC AAG ACT GAC GTG TGC TAC TAC TAC CAG AAG TTC      2160
Leu Pro Ser Lys Arg Lys Thr Asp Val Cys Tyr Tyr Tyr Gln Lys Phe
705                 710                 715                 720

TTC GAT AGT GCC TGC ACG ATG GGT GCC TAC CAC CCG CTG CTC TAT GAG      2208
Phe Asp Ser Ala Cys Thr Met Gly Ala Tyr His Pro Leu Leu Tyr Glu
                725                 730                 735

AAG AAT TTG GTG AAG CAT CTC AAC CAG GGC ACA GAT GAG GAC ATC TAC      2256
Lys Asn Leu Val Lys His Leu Asn Gln Gly Thr Asp Glu Asp Ile Tyr
            740                 745                 750

CTG CTT GGA AAA GCC ACA CTG CCT GGC TTC CGG ACC ATT CAC TGC          2301
Leu Leu Gly Lys Ala Thr Leu Pro Gly Phe Arg Thr Ile His Cys
        755                 760                 765

TAA                                                                   2304
```

( 2 ) INFORMATION FOR SEQ ID NO: 8:

( i ) SEQUENCE CHARACTERISTICS:
        ( A ) LENGTH: 767 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 8:

```
Met Arg Leu Arg Glu Pro Leu Leu Ser Gly Ser Ala Ala Met Pro Gly
1               5                   10                  15

Ala Ser Leu Gln Arg Ala Cys Arg Leu Val Ala Val Cys Ala Leu
            20                  25                  30

His Leu Gly Val Thr Leu Val Tyr Tyr Leu Ala Gly Arg Asp Leu Ser
        35                  40                  45

Arg Leu Pro Gln Leu Val Gly Val Ser Thr Pro Leu Gln Gly Gly Ser
    50                  55                  60

Asn Ser Ala Ala Ala Ile Gly Gln Ser Ser Gly Glu Leu Arg Thr Gly
65                  70                  75                  80

Gly Ala Arg Pro Pro Pro Leu Gly Ala Ser Ser Gln Pro Arg Pro
                85                  90                  95

Gly Gly Asp Ser Ser Pro Val Val Asp Ser Gly Pro Gly Pro Ala Ser
                100                 105                 110

Asn Leu Thr Ser Val Pro Val Pro His Thr Thr Ala Leu Ser Leu Pro
            115                 120                 125

Ala Cys Pro Glu Glu Ser Pro Leu Leu Val Gly Pro Met Leu Ile Glu
```

|     |     |     | 130 |     |     |     |     | 135 |     |     |     |     | 140 |     |
| --- | --- | --- | --- | --- | --- | --- | --- | --- | --- | --- | --- | --- | --- | --- |

Phe Asn Met Pro Val Asp Leu Glu Leu Val Ala Lys Gln Asn Pro Asn
145                 150                 155                 160

Val Lys Met Gly Gly Arg Tyr Ala Pro Arg Asp Cys Val Ser Pro His
            165                 170                 175

Lys Val Ala Ile Ile Ile Pro Phe Arg Asn Arg Gln Glu His Leu Lys
            180                 185                 190

Tyr Trp Leu Tyr Tyr Leu His Pro Val Leu Gln Arg Gln Gln Leu Asp
        195                 200                 205

Tyr Gly Ile Tyr Val Ile Asn Gln Ala Gly Asp Thr Ile Phe Asn Arg
        210                 215                 220

Ala Lys Leu Leu Asn Val Gly Phe Gln Glu Ala Leu Lys Asp Tyr Asp
225                 230                 235                 240

Tyr Thr Cys Phe Val Phe Ser Asp Val Asp Leu Ile Pro Met Asn Asp
                245                 250                 255

His Asn Ala Tyr Arg Cys Phe Ser Gln Pro Arg His Ile Ser Val Ala
            260                 265                 270

Met Asp Lys Phe Gly Phe Ser Leu Pro Tyr Val Gln Tyr Phe Gly Gly
        275                 280                 285

Val Ser Ala Leu Ser Lys Gln Gln Phe Leu Thr Ile Asn Gly Phe Pro
290                 295                 300

Asn Asn Tyr Trp Gly Trp Gly Gly Glu Asp Asp Asp Ile Phe Asn Arg
305                 310                 315                 320

Leu Val Phe Arg Gly Met Ser Ile Ser Arg Pro Asn Ala Val Val Gly
                325                 330                 335

Arg Cys Arg Met Ile Arg His Ser Arg Asp Lys Lys Asn Glu Pro Asn
            340                 345                 350

Pro Gln Arg Phe Asp Arg Ile Ala His Thr Lys Glu Thr Met Leu Ser
        355                 360                 365

Asp Gly Leu Asn Ser Leu Thr Tyr Gln Val Leu Asp Val Gln Arg Tyr
        370                 375                 380

Pro Leu Tyr Thr Gln Ile Thr Val Asp Ile Gly Thr Arg Ala Arg Ile
385                 390                 395                 400

Arg Arg Pro Ala Glu Phe Gln Val Leu Lys Ser Leu Gly Lys Leu Ala
                405                 410                 415

Met Gly Ser Asp Ser Gln Ser Val Ser Ser Ser Thr Gln Asp Pro
            420                 425                 430

His Arg Gly Arg Gln Thr Leu Gly Ser Leu Arg Gly Leu Ala Lys Ala
        435                 440                 445

Lys Pro Glu Ala Ser Phe Gln Val Trp Asn Lys Asp Ser Ser Ser Lys
450                 455                 460

Asn Leu Ile Pro Arg Leu Gln Lys Ile Trp Lys Asn Tyr Leu Ser Met
465                 470                 475                 480

Asn Lys Tyr Lys Val Ser Tyr Lys Gly Pro Gly Pro Gly Ile Lys Phe
            485                 490                 495

Ser Ala Glu Ala Leu Arg Cys His Leu Arg Asp His Val Asn Val Ser
            500                 505                 510

Met Val Glu Val Thr Asp Phe Pro Phe Asn Thr Ser Glu Trp Glu Gly
        515                 520                 525

Tyr Leu Pro Lys Glu Ser Ile Arg Thr Lys Ala Gly Pro Trp Gly Arg
        530                 535                 540

Cys Ala Val Val Ser Ser Ala Gly Ser Leu Lys Ser Ser Gln Leu Gly
545                 550                 555                 560

-continued

| | | | | | | | | | | | | | | |
|---|---|---|---|---|---|---|---|---|---|---|---|---|---|---|
| Arg | Glu | Ile | Asp | Asp 565 | His | Asp | Ala | Val | Leu 570 | Arg | Phe | Asn | Gly | Ala 575 | Pro |
| Thr | Ala | Asn | Phe 580 | Gln | Gln | Asp | Val | Gly 585 | Thr | Lys | Thr | Thr | Ile 590 | Arg | Leu |
| Met | Asn | Ser 595 | Gln | Leu | Val | Thr | Thr 600 | Glu | Lys | Arg | Phe | Leu 605 | Lys | Asp | Ser |
| Leu | Tyr 610 | Asn | Glu | Gly | Ile | Leu 615 | Ile | Val | Trp | Asp | Pro 620 | Ser | Val | Tyr | His |
| Ser 625 | Asp | Ile | Pro | Lys | Trp 630 | Tyr | Gln | Asn | Pro | Asp 635 | Tyr | Asn | Phe | Phe | Asn 640 |
| Asn | Tyr | Lys | Thr | Tyr 645 | Arg | Lys | Leu | His | Pro 650 | Asn | Gln | Pro | Phe | Tyr 655 | Ile |
| Leu | Lys | Pro | Gln 660 | Met | Pro | Trp | Glu | Leu 665 | Trp | Asp | Ile | Leu | Gln 670 | Glu | Ile |
| Ser | Pro | Glu 675 | Glu | Ile | Gln | Pro | Asn 680 | Pro | Pro | Ser | Ser | Gly 685 | Met | Leu | Gly |
| Ile | Ile 690 | Ile | Met | Met | Thr | Leu 695 | Cys | Asp | Gln | Val | Asp 700 | Ile | Tyr | Glu | Phe |
| Leu 705 | Pro | Ser | Lys | Arg | Lys 710 | Thr | Asp | Val | Cys | Tyr 715 | Tyr | Tyr | Gln | Lys | Phe 720 |
| Phe | Asp | Ser | Ala | Cys 725 | Thr | Met | Gly | Ala | Tyr 730 | His | Pro | Leu | Leu | Tyr 735 | Glu |
| Lys | Asn | Leu | Val 740 | Lys | His | Leu | Asn | Gln 745 | Gly | Thr | Asp | Glu | Asp 750 | Ile | Tyr |
| Leu | Leu | Gly 755 | Lys | Ala | Thr | Leu | Pro 760 | Gly | Phe | Arg | Thr | Ile 765 | His | Cys | |